US010588988B2

(12) United States Patent
Robinson et al.

(10) Patent No.: US 10,588,988 B2
(45) Date of Patent: Mar. 17, 2020

(54) METHODS AND DEVICES FOR PREPARATION OF ULTRASOUND CONTRAST AGENTS

(71) Applicant: Lantheus Medical Imaging, Inc., North Billerica, MA (US)

(72) Inventors: Simon P. Robinson, Stow, MA (US); Carol Walker, Billerica, MA (US); David C. Onthank, Groton, MA (US); Joel Lazewatsky, Auburndale, MA (US); Nhung Tuyet Nguyen, Westford, MA (US)

(73) Assignee: Lantheus Medical Imaging, Inc., North Billerica, MA (US)

( * ) Notice: Subject to any disclaimer, the term of this patent is extended or adjusted under 35 U.S.C. 154(b) by 0 days.

(21) Appl. No.: 16/559,528

(22) Filed: Sep. 3, 2019

(65) Prior Publication Data
US 2020/0000943 A1   Jan. 2, 2020

Related U.S. Application Data

(63) Continuation of application No. 15/587,368, filed on May 4, 2017.

(60) Provisional application No. 62/332,462, filed on May 5, 2016, provisional application No. 62/331,968, filed on May 4, 2016.

(51) Int. Cl.
*A61K 49/22* (2006.01)
*A61K 9/50* (2006.01)
*A61K 47/10* (2017.01)
*A61B 8/13* (2006.01)

(52) U.S. Cl.
CPC .............. *A61K 49/22* (2013.01); *A61K 9/50* (2013.01); *A61K 49/227* (2013.01); *A61B 8/13* (2013.01); *A61K 47/10* (2013.01)

(58) Field of Classification Search
None
See application file for complete search history.

(56) References Cited

U.S. PATENT DOCUMENTS

| | | |
|---|---|---|
| 3,873,564 A | 3/1975 | Schneider et al. |
| 4,089,801 A | 5/1978 | Schneider |
| 4,224,179 A | 9/1980 | Schneider |
| 4,229,360 A | 10/1980 | Schneider et al. |
| 5,045,304 A | 9/1991 | Schneider et al. |
| 5,053,217 A | 10/1991 | Lehigh |
| 5,088,499 A | 2/1992 | Unger |
| 5,123,414 A | 6/1992 | Unger |
| 5,149,319 A | 9/1992 | Unger |
| 5,205,290 A | 4/1993 | Unger |
| 5,209,720 A | 5/1993 | Unger |
| 5,228,446 A | 7/1993 | Unger et al. |
| 5,230,882 A | 7/1993 | Unger |
| 5,271,928 A | 12/1993 | Schneider et al. |
| 5,281,408 A | 1/1994 | Unger |
| 5,305,757 A | 4/1994 | Unger et al. |
| 5,334,381 A | 8/1994 | Unger |
| 5,348,016 A | 9/1994 | Unger et al. |
| 5,352,435 A | 10/1994 | Unger |
| 5,358,702 A | 10/1994 | Unger |
| 5,368,840 A | 11/1994 | Unger |
| 5,380,519 A | 1/1995 | Schneider et al. |
| 5,393,524 A | 2/1995 | Quay |
| 5,409,688 A | 4/1995 | Quay |
| 5,413,774 A | 5/1995 | Schneider et al. |
| 5,445,813 A | 8/1995 | Schneider et al. |
| 5,456,900 A | 10/1995 | Unger |
| 5,456,901 A | 10/1995 | Unger |
| 5,469,854 A | 11/1995 | Unger et al. |
| 5,527,521 A | 6/1996 | Unger |
| 5,531,980 A | 7/1996 | Schneider et al. |
| 5,542,935 A | 8/1996 | Unger et al. |
| 5,547,656 A | 8/1996 | Unger |
| 5,558,092 A | 9/1996 | Unger et al. |
| 5,558,094 A | 9/1996 | Quay |
| 5,558,853 A | 9/1996 | Quay |
| 5,558,854 A | 9/1996 | Quay |
| 5,558,855 A | 9/1996 | Quay |
| 5,567,414 A | 10/1996 | Schneider et al. |
| 5,571,497 A | 11/1996 | Unger |
| 5,573,751 A | 11/1996 | Quay |
| 5,578,292 A | 11/1996 | Schneider et al. |
| 5,580,575 A | 12/1996 | Unger et al. |
| 5,585,112 A | 12/1996 | Unger et al. |
| 5,595,723 A | 1/1997 | Quay |
| 5,643,553 A | 7/1997 | Schneider et al. |
| 5,656,211 A | 8/1997 | Unger et al. |

(Continued)

FOREIGN PATENT DOCUMENTS

| | | |
|---|---|---|
| CN | 101229382 A | 7/2008 |
| DE | 38 03 972 A1 | 8/1989 |

(Continued)

OTHER PUBLICATIONS

International Search Report and Written Opinion dated Nov. 29, 2017 for PCT/US2017/031150.
International Preliminary Report on Patentability dated Nov. 15, 2018 for PCT/US2017/031150.
[No Author Listed] Definity FDA Approval Label. Initial US Approval: 2001. U.S. Food and Drug Administration. Silver Spring, Maryland. Revised Aug. 2015. 19 pages.
[No Author Listed] Division of new drug chemistry document relating to Definity. Review date, Feb. 15, 2001.
[No Author Listed] EMEA Scientific discussion relating to Sonovue. Updated until Oct. 1, 2004. 1 page.
[No Author Listed] http://www.acusphere.com/product/prod/_imagify.html. In existence as of Apr. 29, 2009. 1 page.
[No Author Listed], VIALMIX User's Guide. Lantheus Medical Imaging. North Billerica, MA. Aug. 2010. 42 pages.

(Continued)

*Primary Examiner* — Jennifer Lamberski
(74) *Attorney, Agent, or Firm* — Wolf, Greenfield & Sacks, P.C.

(57) ABSTRACT

Provided herein are methods and devices for identifying and/or distinguishing UCA formulations and specifically activating such formulations to produce UCA suitable for in vivo use.

28 Claims, 7 Drawing Sheets

(56) References Cited

U.S. PATENT DOCUMENTS

| | | | |
|---|---|---|---|
| 5,686,060 | A | 11/1997 | Schneider et al. |
| 5,705,187 | A | 1/1998 | Unger |
| 5,707,606 | A | 1/1998 | Quay |
| 5,707,607 | A | 1/1998 | Quay |
| 5,715,824 | A | 2/1998 | Unger et al. |
| 5,733,572 | A | 3/1998 | Unger et al. |
| 5,736,121 | A | 4/1998 | Unger |
| 5,738,869 | A | 4/1998 | Fischer et al. |
| 5,769,080 | A | 6/1998 | Unger et al. |
| 5,770,222 | A | 6/1998 | Unger et al. |
| 5,773,024 | A | 6/1998 | Unger et al. |
| 5,776,429 | A | 7/1998 | Unger et al. |
| 5,776,488 | A | 7/1998 | Mori et al. |
| 5,830,430 | A | 11/1998 | Unger et al. |
| 5,843,473 | A | 12/1998 | Woodle et al. |
| 5,846,517 | A | 12/1998 | Unger |
| 5,853,752 | A | 12/1998 | Unger et al. |
| 5,853,755 | A | 12/1998 | Foldvari |
| 5,874,062 | A | 2/1999 | Unger |
| 5,897,851 | A | 4/1999 | Quay et al. |
| 5,922,304 | A | 7/1999 | Unger |
| 5,935,553 | A | 8/1999 | Unger et al. |
| 5,985,246 | A | 11/1999 | Unger |
| 5,997,898 | A | 12/1999 | Unger |
| 6,001,335 | A | 12/1999 | Unger |
| 6,028,066 | A | 2/2000 | Unger |
| 6,033,645 | A | 3/2000 | Unger et al. |
| 6,033,646 | A | 3/2000 | Unger et al. |
| 6,039,557 | A | 3/2000 | Unger et al. |
| 6,056,938 | A | 5/2000 | Unger et al. |
| 6,066,331 | A | 5/2000 | Barenholz et al. |
| 6,071,494 | A | 6/2000 | Unger et al. |
| 6,071,495 | A | 6/2000 | Unger et al. |
| 6,088,613 | A | 7/2000 | Unger |
| 6,090,800 | A | 7/2000 | Unger et al. |
| 6,117,414 | A | 9/2000 | Unger |
| 6,120,794 | A | 9/2000 | Liu et al. |
| 6,123,923 | A | 9/2000 | Unger et al. |
| 6,139,819 | A | 10/2000 | Unger et al. |
| 6,143,276 | A | 11/2000 | Unger |
| 6,146,657 | A | 11/2000 | Unger et al. |
| 6,214,375 | B1 | 4/2001 | Modi |
| 6,231,834 | B1 | 5/2001 | Unger et al. |
| 6,258,378 | B1 | 7/2001 | Schneider et al. |
| 6,315,981 | B1 | 11/2001 | Unger |
| 6,414,139 | B1 | 7/2002 | Unger et al. |
| 6,416,740 | B1 | 7/2002 | Unger |
| 6,443,898 | B1 | 9/2002 | Unger et al. |
| 6,444,660 | B1 | 9/2002 | Unger et al. |
| 6,461,586 | B1 | 10/2002 | Unger |
| 6,479,034 | B1 | 11/2002 | Unger et al. |
| 6,521,211 | B1 | 2/2003 | Unger et al. |
| 6,528,039 | B2 | 3/2003 | Unger |
| 6,537,246 | B1 | 3/2003 | Unger et al. |
| 6,548,047 | B1 | 4/2003 | Unger |
| 6,551,576 | B1 | 4/2003 | Unger et al. |
| 6,572,840 | B1 | 6/2003 | Toler |
| 6,576,220 | B2 | 6/2003 | Unger |
| 6,716,412 | B2 | 4/2004 | Unger |
| 6,773,696 | B2 | 8/2004 | Unger |
| 6,884,407 | B1 | 4/2005 | Unger |
| 6,943,692 | B2 | 9/2005 | Castner et al. |
| 6,998,107 | B2 | 2/2006 | Unger |
| 7,344,705 | B2 | 3/2008 | Unger |
| 7,859,473 | B2 | 12/2010 | Gibson |
| 8,084,056 | B2 | 12/2011 | Hui et al. |
| 8,658,205 | B2 | 2/2014 | Hui et al. |
| 8,685,441 | B2 | 4/2014 | Hui et al. |
| 8,747,892 | B2 | 6/2014 | Hui et al. |
| 9,545,457 | B2 | 1/2017 | Hui et al. |
| 9,789,210 | B1 | 10/2017 | Robinson et al. |
| 9,913,919 | B2 | 3/2018 | Robinson et al. |
| 10,022,460 | B2 | 7/2018 | Robinson et al. |
| 10,220,104 | B2 | 3/2019 | Robinson et al. |
| 2003/0044354 | A1 | 3/2003 | Carpenter, Jr. et al. |
| 2004/0057991 | A1 | 3/2004 | Hui et al. |
| 2005/0163716 | A1 | 7/2005 | Unger et al. |
| 2007/0071685 | A1 | 3/2007 | Schneider et al. |
| 2008/0009561 | A1 | 1/2008 | Unger et al. |
| 2008/0118435 | A1 | 5/2008 | Unger |
| 2010/0089803 | A1 | 4/2010 | Lavi et al. |
| 2010/0222921 | A1 | 9/2010 | Harre et al. |
| 2012/0027688 | A1 | 2/2012 | Hui et al. |
| 2012/0035063 | A1 | 2/2012 | Kim et al. |
| 2012/0097702 | A1 | 4/2012 | Harre et al. |
| 2012/0128595 | A1 | 5/2012 | Hui et al. |
| 2012/0263009 | A1* | 10/2012 | Lim .................. B01F 11/0065 366/108 |
| 2013/0022550 | A1 | 1/2013 | Unger et al. |
| 2013/0123781 | A1 | 5/2013 | Grubbs et al. |
| 2013/0309174 | A1 | 11/2013 | Hui et al. |
| 2013/0309175 | A1 | 11/2013 | Hui et al. |
| 2014/0328767 | A1 | 11/2014 | Wang |
| 2016/0000943 | A1 | 1/2016 | Unger et al. |
| 2016/0030596 | A1 | 2/2016 | Kheir et al. |
| 2016/0331851 | A1 | 11/2016 | Robinson et al. |
| 2017/0258946 | A1 | 9/2017 | Robinson et al. |
| 2017/0312375 | A1 | 11/2017 | Hui et al. |
| 2017/0319718 | A1 | 11/2017 | Robinson et al. |
| 2017/0360966 | A1 | 12/2017 | Robinson et al. |
| 2018/0008732 | A1 | 1/2018 | Robinson et al. |
| 2018/0221516 | A1 | 8/2018 | Robinson et al. |
| 2019/0142978 | A1 | 5/2019 | Robinson et al. |
| 2019/0201559 | A1 | 7/2019 | Robinson et al. |
| 2019/0255197 | A1 | 8/2019 | Robinson et al. |

FOREIGN PATENT DOCUMENTS

| | | |
|---|---|---|
| EP | 0 052 575 A2 | 5/1982 |
| EP | 0 077 752 A2 | 4/1983 |
| EP | 0 224 934 A2 | 6/1987 |
| EP | 0 231 091 A1 | 8/1987 |
| EP | 0 274 961 A1 | 7/1988 |
| EP | 0 314 764 A1 | 5/1989 |
| EP | 0 324 938 A1 | 7/1989 |
| EP | 0 338 971 A1 | 10/1989 |
| EP | 0 349 429 A2 | 1/1990 |
| EP | 0 458 745 A1 | 11/1991 |
| EP | 0 554 213 A1 | 8/1993 |
| EP | 0 901 793 A1 | 3/1999 |
| EP | 0 957 942 A2 | 11/1999 |
| JP | 63-60943 | 3/1988 |
| JP | 63-277618 A | 11/1988 |
| JP | 2-149336 A | 6/1990 |
| JP | 8-151335 A | 6/1996 |
| WO | WO 80/02365 A1 | 11/1980 |
| WO | WO 82/01642 A1 | 5/1982 |
| WO | WO 85/02772 A1 | 7/1985 |
| WO | WO 89/10118 A1 | 11/1989 |
| WO | WO 90/04384 A1 | 5/1990 |
| WO | WO 90/14846 A1 | 12/1990 |
| WO | WO 91/00086 A1 | 1/1991 |
| WO | WO 91/09629 A1 | 7/1991 |
| WO | WO 91/15244 A2 | 10/1991 |
| WO | WO 91/15753 A1 | 10/1991 |
| WO | WO 92/10166 A1 | 6/1992 |
| WO | WO 92/15284 A1 | 9/1992 |
| WO | WO 92/17212 A1 | 10/1992 |
| WO | WO 92/17514 A1 | 10/1992 |
| WO | WO 92/22247 A1 | 12/1992 |
| WO | WO 92/22249 A1 | 12/1992 |
| WO | WO 92/22298 A1 | 12/1992 |
| WO | WO 93/05819 A1 | 4/1993 |
| WO | WO 93/06869 A1 | 4/1993 |
| WO | WO 93/13802 A1 | 7/1993 |
| WO | WO 94/09829 A1 | 5/1994 |
| WO | WO 94/16739 A1 | 8/1994 |
| WO | WO 94/21301 A1 | 9/1994 |
| WO | WO 94/21302 A1 | 9/1994 |
| WO | WO 94/28780 A2 | 12/1994 |
| WO | WO 94/28797 A1 | 12/1994 |
| WO | WO 94/28873 A1 | 12/1994 |
| WO | WO 94/28874 A1 | 12/1994 |
| WO | WO 95/03835 A1 | 2/1995 |

(56) References Cited

FOREIGN PATENT DOCUMENTS

| | | |
|---|---|---|
| WO | WO 95/06518 A1 | 3/1995 |
| WO | WO 95/07072 A2 | 3/1995 |
| WO | WO 95/12387 A1 | 5/1995 |
| WO | WO 95/15118 A1 | 6/1995 |
| WO | WO 95/16467 A1 | 6/1995 |
| WO | WO 95/23615 A1 | 9/1995 |
| WO | WO 95/24184 A1 | 9/1995 |
| WO | WO 95/26205 A1 | 10/1995 |
| WO | WO 95/32005 A1 | 11/1995 |
| WO | WO 95/32006 A1 | 11/1995 |
| WO | WO 96/04018 A1 | 2/1996 |
| WO | WO 96/08234 A1 | 3/1996 |
| WO | WO 96/09793 A1 | 4/1996 |
| WO | WO 96/31196 A1 | 10/1996 |
| WO | WO 96/40281 A2 | 12/1996 |
| WO | WO 96/40285 A1 | 12/1996 |
| WO | WO 97/00638 A2 | 1/1997 |
| WO | WO 97/40679 A1 | 11/1997 |
| WO | WO 97/40858 A1 | 11/1997 |
| WO | WO 97/48337 A1 | 12/1997 |
| WO | WO 98/04292 A2 | 2/1998 |
| WO | WO 98/10798 A1 | 3/1998 |
| WO | WO 98/10799 A1 | 3/1998 |
| WO | WO 98/17324 A2 | 4/1998 |
| WO | WO 98/18495 A2 | 5/1998 |
| WO | WO 98/18498 A2 | 5/1998 |
| WO | WO 98/18500 A2 | 5/1998 |
| WO | WO 98/18501 A2 | 5/1998 |
| WO | WO 98/42384 A1 | 10/1998 |
| WO | WO 98/51284 A1 | 11/1998 |
| WO | WO 99/08714 A1 | 2/1999 |
| WO | WO 99/13919 A1 | 3/1999 |
| WO | WO 99/30620 A1 | 6/1999 |
| WO | WO 99/36104 A2 | 7/1999 |
| WO | WO 99/39738 A1 | 8/1999 |
| WO | WO 00/45856 A2 | 8/2000 |
| WO | WO 2004/030617 A1 | 4/2004 |
| WO | WO 2013/013067 A2 | 1/2013 |

OTHER PUBLICATIONS

[No Author Listed], CapMix Capsule Mixing Device Product Information Sheet. 3M ESPE. Seefeld, Germany. 2004. 2 pages.

[No Author Listed], Crescent Wig-L-Bug Product Information Sheet. Dentsply Rinn. York, PA. Oct. 2014. 2 pages.

[No Author Listed], Liposome Drug Products—Chemistry, Manufacturing, and Controls; Human Pharmacokinetics and Bioavailability; and Labeling Documentation—Guidance for Industry—Draft Guidance. U.S. Department of Health and Human Services, Food and Drug Administration, Center for Drug Evaluation and Research. Silver Spring, MD. Oct. 2015. 17 pages.

Almansouri et al., Alternative power source for dental hygiene device. 2012 Project Proposal. Department of Mechanical Engineering Northern Arizona University. 2012. Accessed Oct. 29, 2018 from <cefns.nau.edu/capstone/projects/ME/2013/Concussion/report4.pdf>. 18 pages.

Bedu-Addo, F.K., et al., "Effects of polyethyleneglycol chain length and phospholipids acyl chain composition on the interaction of polyethyleneglycol-phospholipid conjugants with phospholipids: implications in liposomal drug delivery," Pharm. Res., May 1996, 13(5), 710-717.

Belsito, S., et al., "Sterically stabilized liposomes of DPPC/DPPE-PEG 2000—A spin label ESR & spectrophotometric study," Biophysical Chem., May 10, 1998, 75(1), 33-43.

Blomley et al., "Microbubble contrast agents: a new era in ultrasound"; Clinical Review XP008001399, BMJ, vol. 322, pp. 1222-1225 (May 19, 2001).

Chapman, Physicochemical properties of Phospholipids and Lipid-Water Systems. Liposome Technology: Preparation of Liposomes—Chapter 1. Gregory Gregoriadis, Ed. CRC Press, Boca Raton, FL. 1984;1:1-18.

De Jong et al., New ultrasound contrast agents and technological innovations. Ultrasonics. Jun. 1996;34(2-5):587-90.

Deamer, Preparation of Solvent Vaporization Liposomes. Liposome Technology: Preparation of Liposomes—Chapter 3. Gregory Gregoriadis, Ed. CRC Press, Boca Raton, FL. 1984;1:29-35.

Feinstein et al., "Two-Dimensional Contrast Echocardiography. I. In Vitro Development and Quantitative Analysis of Echo Contrast Agents", JACC, vol. 3, No. 1, pp. 14-20 (1984).

Fritz et al., Phase I clinical trials of MRX-115. A new ultrasound contrast agent. Invest Radiol. Dec. 1997;32(12):735-40.

Fritz et al., Preclinical Studies of MRX-115: Safety Evaluations of a Myocardial Perfusion Agent. Acad. Radiol. Aug. 1996;3(Suppl 2):S185-7.

Fritzsch et al., "Preclinical and Clinical Results with an Ultrasonic Contrast Agent", Inv. Rad., vol. 23, pp. S302-S305, Sep. 1988.

Gabizon et al., "Liposome formulations with prolonged circulation time in blood and enhanced uptake by tumors", Proc. Natl. Acad. Sci., vol. 85, pp. 6949-6953 (1988).

Goldberg, et al., "Ultrasound contrast agents: a review," Ultrasound in Med. & Biol., 1994, 20(4), 319-333.

Gross, U. et al., "Phosholipid vesiculated fluorocarbons promising trend in blood substitutes" Biomat., Art. Cells & Immob Biotech., 1992, vol. 20, (2-4) pp. 831-833.

Hettiarachchi et al., On-chip generation of microbubbles as a practical technology for manufacturing contrast agents for ultrasonic imaging. Lab Chip. Apr. 2007;7(4):463-8. Epub Mar. 8, 2007.

Hope et al., "Generation of Multilamellar and Unilamellar Phospholipid Vesicles", Chemistry and Physics of Lipids, vol. 40, pp. 89-107 (1986).

Ishida et al., Accelerated clearance of PEGylated liposomes in rats after repeated injections. J Control Release. Feb. 14, 2003;88(1):35-42.

Kitzman et al., Efficacy and safety of the novel ultrasound contrast agent perflutren (DEFINITY) in patients with suboptimal baseline left ventricular echocardiographic images. Am J Cardiol. Sep. 15, 2000;86(6):669-74.

Klibanov, Preparation of targeted microbubbles: ultrasound contrast agents for molecular imaging. Med. Biol. Eng. Comput. 2009;47:875-82.

Lelkes, The Use of French Pressed Vesicles for Efficient Incorporation of Bioactive Macromolecules and as Drug Carriers In Vitro and In Vivo. Liposome Technology: Preparation of Liposomes—Chapter 5. Gregory Gregoriadis, Ed. CRC Press, Boca Raton, FL. 1984;1:51-65.

Metzger-Rose et al., Ultrasonographic Detection of Testicular Ischemia in a Canine Model Using Phospholipid Coated Microbubbles (MRX-115). J. Ultrasound Med. 1997;16:317-24.

Nikolova, A., et al., "Effect of grafted PEG-2000 on the size and permeability of vesicles," Biochim Biophys Acta, Nov. 22, 1996, 1304(2), 120-128.

Ohki, et al., "Short & long range calcium-induced lateral phase separations in ternary mixtures of phosphatidic acid phosphatidylcholine and phosphatidylethanolamine," Chem. & Physics of Lipids, 1989, 50(2), 109-118.

Ophir et al., "Contrast Agents in Diagnostic Ultrasound", Ultrasound in Med. & Biol., vol. 15, No. 4, pp. 319-333 (1989).

Sarkar et al., Growth and dissolution of an encapsulated contrast microbubble: effects of encapsulation permeability. Ultrasound Med Biol. Aug. 2009;35(8):1385-96. doi: 10.1016/j.ultrasmedbio.2009.04.010.

Schutt et al., "Osmotically Stabilized Microbubble Sonographic Contrast Agents", Acad. Radiol., vol. 3, Suppl. 2, pp. S188-S190 (Aug. 1996).

Senior et al., Investigators. Detection of coronary artery disease with perfusion stress echocardiography using a novel ultrasound imaging agent: two Phase 3 international trials in comparison with radionuclide perfusion imaging. Eur J Echocardiogr. Jan. 2009;10(1):26-35.

Senior, Imagify (perflubutane polymer microspheres) injectable suspension for the assessment of coronary artery disease. Expert Rev Cardiovasc Ther. May 2007;5(3):413-21.

(56) References Cited

OTHER PUBLICATIONS

Swanson et al., "Enhancement Agents for Ultrasound: Fundamentals", Pharmaceuticals in Medical Imaging, Chapter 22, pp. 682-687 (1990).
Szoka, et al., "Comparative properties and methods of preparation of liqid vesicles (Liposomes)," Ann. Rev. Biophys. Bioeng., 1980,9, 467-508.
Unger et al., "Gas filled lipid bilayers as imaging contrast agents," J. Liposome Res., 1994, 4(2), 861-874.
Unger et al., "Gas-filled lipid bilayers as ultrasound contrast agent," Invest. Radiol., 1994, 29S2, S134-S136.
Unger et al., "Hepatic Metastases: Liposomal Gd-DTPA-enhanced MR Imaging", Radiology, vol. 171, No. 1, pp. 81-85 (1989).
Unger et al., "In Vitro Studies of a New Thrombus-Specific Ultrasound Contrast Agent", American Journal of Cardiology, vol. 81, No. 12, Suppl. A, pp. 58G-61G, XP-002087505, Jun. 12, 1998 and Symposium: Ninth International Congress on Echocardiography: Clinical Cardiology, 1997.
Unger et al., "Liposomal MR Contrast Agents", J. Liposome Research, 4(2), pp. 811-834 (1994).
Unger et al., Gas-Filled Liposomes as Echocardiographic Contrast Agents in Rabbits with Myocardial Infarcts. Investigative Radiology. Dec. 1993;28(12):1155-9.
Unger et al., Nitrogen-filled Liposomes as a Vascular US Contrast Agent: Preliminary Evaluation. Radiology. Nov. 1992;185:453-6.
Unger et al., Therapeutic applications of lipid-coated microbubbles. Advanced Drug Delivery Reviews. 2004;56:1291-1314.
Wang et al., Anti-PEG IgM elicited by injection of liposomes is involved in the enhanced blood clearance of a subsequent dose of PEGylated liposomes. J Control Release. Jun. 4, 2007;119(2):236-44. Epub Feb. 24, 2007.
Weder et al., The Preparation of Variably Sized Homogeneous Liposomes for Laboratory, Clinical, and Industrial Use by Controlled Detergent Dialysis. Liposome Technology: Preparation of Liposomes—Chapter 7. Gregory Gregoriadis, Ed. CRC Press, Boca Raton, FL. 1984;1:79-107.
Yuda et al., Prolongation of liposome circulation time by various derivatives of polyethyleneglycols. Biol Pharm Bull. Oct. 1996;19(10):1347-51.
Extended European Search Report for Application No. EP 17793385.0, dated Nov. 25, 2019.

\* cited by examiner

METHODS AND DEVICES FOR PREPARATION OF ULTRASOUND CONTRAST AGENTS

RELATED APPLICATION

This application is a continuation of U.S. application Ser. No. 15/587,368, filed May 4, 2017 which claims the benefit under 35 U.S.C. § 119(e) of U.S. Provisional Application No. 62/331,968, filed on May 4, 2016, and 62/332,462, filed on May 5, 2016, all of which are entitled "METHODS AND DEVICES FOR PREPARATION OF ULTRASOUND CONTRAST AGENTS", the entire contents of each of which are incorporated by reference herein.

COMPUTER PROGRAM LISTING APPENDIX

A computer program listing is appended to this disclosure and is incorporated herein by reference. The appendix contains the file N046970143US03-CPL-MAT.txt, which was created on Feb. 3, 2020, and is 13,507 bytes in size.

BACKGROUND

Contrast-enhanced ultrasound imaging is a commonly used medical imaging modality. Most if not all ultrasound contrast agents (UCA) are gas-filled microspheres that are useful in enhancing ultrasound signal. One such UCA is activated DEFINITY® comprising perflutren lipid microspheres (i.e., perflutren gas encapsulated in lipid microspheres). DEFINITY® formulation is packaged in a vial comprising lipids in an aqueous suspension with perflutren gas in the headspace. Prior to use, DEFINITY® is activated by shaking the vial vigorously, thereby forming lipid microspheres comprising perflutren gas suspended in an aqueous liquid. Proper activation ensures that the microspheres formed are of the appropriate size and concentration to be both diagnostically effective and safe for the subject. Due to the importance of proper size and concentration, activation should optimally be performed in a manner that minimizes the potential for human error.

SUMMARY

This disclosure contemplates methods and devices for ensuring that activation-dependent UCA formulations, such as but not limited to DEFINITY® formulation, are properly distinguished from each other and thus properly activated. As additional activation-dependent UCA formulations come to market, it will be imperative to distinguish between them in order to ensure each is handled and activated in the correct prescribed manner. As an example, each activation-dependent UCA will have its own unique activation parameters, including for example activation time and/or activation rate (e.g., shaking rate), and thus it will be imperative that each UCA formulation be handled in a specific manner. Applying incorrect activation parameters to a UCA formulation can result in a UCA that is not diagnostically useful (e.g., due to a very low concentration or inappropriate size of microspheres), requiring a subject to undergo the ultrasound procedure again. At worst, it can result in microspheres that are too large, and this increases the chance of causing ischemia by occluding capillary beds.

One such new and improved UCA formulation is a non-aqueous UCA formulation, referred to herein as DEFINITY-II. This UCA formulation is surprisingly more robust than earlier liquid UCA formulations. Specifically, unlike earlier liquid UCA formulations which had to be stored cold prior to use, this new non-aqueous UCA formulation is stable at room temperature for extended periods of time. Even more surprisingly, this UCA formulation can be made and used without complex manipulation. Given these added benefits, it is expected that this new non-aqueous UCA formulation will be readily adopted. The formulation is however activated for a different time period than the DEFINITY® formulation, and therefore it is important to ensure that each UCA formulation is activated for its own specific optimal period of time. Activation for a different period of time can lead to microspheres that are too large, or too small, and/or of such low concentration to be clinical useful. Given the significant outcomes if the UCA is not prepared properly (e.g., is not activated properly), it is important to have methods and devices that identify and optionally distinguish between specific UCA formulations, such as aqueous DEFINITY® and non-aqueous DEFINITY-II formulations, and apply correct activation parameters to such UCA formulations, preferably with minimal dependence on human intervention.

Thus, this disclosure provides in one aspect, a method for forming gas-filled microspheres comprising identifying a UCA formulation, and activating the UCA formulation for a pre-determined (e.g., pre-set) period of time using a device that selects between two or more pre-determined periods of time, to form gas-filled microspheres. The device may automatically select between the two or more pre-determined periods of time. In some embodiments, the means is also able to identify the UCA formulation and/or its housing (e.g., container, such as vial), and optionally distinguish such UCA formulation and/or its housing form one or more other UCA formulations or housings.

This disclosure provides, in another aspect, a method for forming gas-filled microspheres comprising identifying a UCA formulation, and activating the UCA formulation using a pre-determined shaking rate using a device that selects between two or more pre-determined shaking rates, to form gas-filled microspheres.

This disclosure provides, in another aspect, a method for forming gas-filled microspheres comprising activating a UCA formulation to form gas-filled microspheres, using a means (e.g., a device) that distinguishes an aqueous UCA formulation from a non-aqueous UCA formulation (and/or vice versa). The aqueous UCA formulation may be distinguished from a non-aqueous UCA formulation (or vice versa) based on the type of container including its shape or size housing such UCA formulations.

In some embodiments of any of the foregoing aspects, the means (e.g., device) comprises a detector. In some embodiments of any of the foregoing aspects and embodiments, the means (e.g., device) is able to activate at a pre-determined period of time selected between two or more pre-determined periods of time.

This disclosure provides, in another aspect, a method for forming gas-filled microspheres comprising identifying a UCA formulation requiring activation for a pre-determined period of time, using a means (e.g., device) that distinguishes an aqueous UCA formulation from a non-aqueous UCA formulation, and activating the UCA formulation for a pre-determined period of time to form gas-filled microspheres.

In some embodiments of any of the foregoing aspects and embodiments, the UCA formulation is an aqueous UCA formulation. In some embodiments of any of the foregoing aspects and embodiments, the UCA formulation is a non-aqueous UCA formulation.

In some embodiments of any of the foregoing aspects and embodiments, the pre-determined period of time is a shorter period of time if the UCA formulation is an aqueous UCA formulation and a longer period of time if the UCA formulation is a non-aqueous UCA formulation. In some embodiments of any of the foregoing aspects and embodiments, the pre-determined period of time is about 45 seconds if the UCA formulation is an aqueous UCA formulation and 60-120 seconds or about 75 seconds if the UCA formulation is a non-aqueous UCA formulation.

In some embodiments of any of the foregoing aspects and embodiments, the device comprises a first holder capable of holding a vial comprising an aqueous UCA formulation and incapable of holding a vial comprising a non-aqueous UCA formulation. In some embodiments of any of the foregoing aspects and embodiments, the device comprises a first holder capable of holding a vial comprising an non-aqueous UCA formulation and incapable of holding a vial comprising a aqueous UCA formulation.

In some embodiments of any of the foregoing aspects and embodiments, the device distinguishes an aqueous UCA formulation from a non-aqueous UCA formulation based on a unique identifier.

In some embodiments of any of the foregoing aspects and embodiments, the device comprises a detector. In some embodiments, the detector is an RFID reader and the UCA formulation is housed in a container that comprises, contains or is associated with or labeled with an RFID tag/label. In some embodiments, the detector is a barcode scanner and the UCA formulation is housed in a container that comprises, contains or is associated with or labeled with a barcode. In some embodiments, the detector is a color scanner and the UCA formulation is housed in a container that comprises a colored label.

In some embodiments of any of the foregoing aspects and embodiments, the device imparts a reciprocating motion to a vial comprising the UCA formulation.

This disclosure provides, in another aspect, a method for forming gas-filled microspheres comprising identifying a labeled vial comprising a UCA formulation requiring activation for a pre-determined period of time, and activating the UCA formulation using a shaking device comprising a detector and set to the pre-determined period of time or capable of automatically selecting the pre-determined period of time based on the identity of the vial, to form gas-filled microspheres.

This disclosure provides, in another aspect, a method for forming gas-filled microspheres comprising identifying a labeled vial comprising a UCA formulation requiring activation for a pre-determined period of time, using a shaking device comprising a detector and set to the pre-determined period of time or capable of automatically selecting the pre-determined period of time based on the identity of the vial, and activating the UCA formulation to form gas-filled microspheres.

In some embodiments of any of the foregoing aspects and embodiments, the labeled vial is labeled with a unique identifier.

In some embodiments of any of the foregoing aspects and embodiments, the pre-determined period of time is about 45 seconds.

In some embodiments of any of the foregoing aspects and embodiments, the detector is an RFID reader and the labeled vial comprises an RFID tag/label. In some embodiments of any of the foregoing aspects and embodiments, the detector is a barcode scanner and the labeled vial comprises a barcode. In some embodiments of any of the foregoing aspects and embodiments, the detector is a color scanner and the labeled vial comprises a colored label.

This disclosure provides, in another aspect, a method for forming gas-filled microspheres comprising activating a UCA formulation for the pre-determined period of time to form gas-filled microspheres, wherein the UCA formulation is activated using a shaking device set to activate at least two different pre-determined periods of time or capable of automatically selecting from at least two different pre-determined periods of time based on the identity of the UCA formulation.

This disclosure provides, in another aspect, a method for forming gas-filled microspheres comprising identifying a UCA formulation requiring activation for a pre-determined period of time, and activating the UCA formulation for the pre-determined period of time to form gas-filled microspheres, wherein the UCA formulation is activated using a shaking device set to activate at at least two different pre-determined periods of time or capable of automatically selecting from at least two different pre-determined periods of time based on the identity of the UCA formulation.

This disclosure provides, in another aspect, a method for forming gas-filled microspheres comprising identifying a non-aqueous UCA formulation requiring activation for a pre-determined period of time, and activating the UCA formulation for the pre-determined period of time to form gas-filled microspheres.

In some embodiments of any of the foregoing aspects and embodiments, the UCA formulation is identified and activated using a shaking device set to activate at a pre-determined period of time or capable of automatically selecting a pre-determined period of time based on the identity of the UCA formulation.

In some embodiments of any of the foregoing aspects and embodiments, the pre-determined period of time is about 45 seconds. In some embodiments of any of the foregoing aspects and embodiments, the pre-determined period of time is in the range of 60-120 seconds or about 75 seconds.

This disclosure provides, in another aspect, a method for forming gas-filled microspheres comprising identifying a non-aqueous UCA formulation requiring activation for a pre-determined first period of time, and activating said UCA formulation to form gas-filled microspheres by shaking using a shaking device capable of automatically selecting the first pre-determined period of time from at least two different pre-determined periods of time, based on identity of the UCA formulation.

This disclosure provides, in another aspect, a method for forming gas-filled microspheres comprising identifying a non-aqueous UCA formulation requiring activation for a pre-determined first period of time based on its container, and activating said UCA formulation to form gas-filled microspheres by shaking using a shaking device capable of automatically selecting the first pre-determined period of time from at least two different pre-determined periods of time, based on identity of the container. In some embodiments, the container is a vial.

In some embodiments of any of the foregoing aspects and embodiments, the at least two different pre-determined periods of time are about 45 seconds and about 75 seconds.

In some embodiments of any of the foregoing aspects and embodiments, the device such as the shaking device imparts a reciprocating motion to the container (e.g., the vial) when present in a holder.

In some embodiments of any of the foregoing aspects and embodiments, the shaking device comprises a detector. The detector may be an RFID reader and the vial may comprise, contain, be associated with or be labeled with an RFID tag/label. The detector may be a barcode scanner and the vial may comprise, contain, be associated with or be labeled with a barcode. The detector may be a color scanner and the vial may comprise, contain, be associated with or be labeled with a colored indicator. The colored indicator may comprise a colored label. The colored indicator may comprise a colored cap.

This disclosure provides, in another aspect, a method for forming gas-filled microspheres comprising activating a UCA formulation using a shaking device that identifies the UCA formulation and automatically selects an activation time based thereon, wherein the UCA formulation is identified based on a unique identifier other than shape or size of vial housing the UCA formulation.

This disclosure provides, in another aspect, a method for activating a first UCA formulation using a shaking device that can distinguish a container such as a vial comprising the first UCA formulation from a container such as a vial comprising a second UCA formulation.

This disclosure provides, in another aspect, a method for forming gas-filled microspheres comprising identifying a labeled vial comprising a UCA formulation requiring activation for a pre-determined first period of time, and activating the UCA formulation using a shaking device set to the pre-determined period of time or capable of automatically selecting the first pre-determined period of time from at least two different pre-determined periods of time, based on the identity of the vial, to form gas-filled microspheres.

This disclosure provides, in another aspect, a method for forming gas-filled microspheres comprising identifying a labeled vial comprising a UCA formulation requiring activation for a pre-determined first period of time, and activating the UCA formulation using a shaking device comprising a detector and set to the pre-determined period of time or capable of automatically selecting the first pre-determined period of time from at least two different pre-determined periods of time, based on the identity of the vial, to form gas-filled microspheres.

This disclosure provides, in another aspect, a method for forming gas-filled microspheres comprising identifying a vial comprising a UCA formulation requiring activation for a pre-determined first period of time, and activating the UCA formulation using a shaking device comprising a detector and set to the pre-determined period of time or capable of automatically selecting the first pre-determined period of time from at least two different pre-determined periods of time, based on the identity of the vial, to form gas-filled microspheres.

In some embodiments of any of the foregoing aspects and embodiments, the at least two different pre-determined periods of time are about 45 seconds and about 75 seconds.

In some embodiments of any of the foregoing aspects and embodiments, the method produces substantially similar gas-filled microspheres from a first vial and a second vial provided the first vial is shaken for a first period of time and the second vial is shaken for a second different period of time.

This disclosure provides, in another aspect, a method for forming gas-filled microspheres comprising identifying an aqueous UCA formulation requiring activation for a pre-determined period of time, using a device that distinguishes the aqueous UCA formulation from a non-aqueous UCA formulation, and activating the aqueous UCA formulation for a pre-determined period of time to form gas-filled microspheres.

This disclosure provides, in another aspect, a method for forming gas-filled microspheres comprising identifying a UCA formulation requiring activation for a pre-determined period of time, and activating the UCA formulation for the pre-determined period of time to form gas-filled microspheres, wherein the UCA formulation is identified and activated using a shaking device capable of automatically selecting the pre-determined period of time from at least 2 pre-determined periods of time based on the identity of the UCA formulation.

In some embodiments of any of the foregoing aspects and embodiments, the UCA formulation is an aqueous UCA formulation. In some embodiments of any of the foregoing aspects and embodiments, the UCA formulation is a non-aqueous UCA formulation. In some embodiments of any of the foregoing aspects and embodiments, an aqueous UCA formulation is activated for a shorter period of time than a non-aqueous UCA formulation. In some embodiments of any of the foregoing aspects and embodiments, the pre-determined period of time is about 45 seconds. In some embodiments of any of the foregoing aspects and embodiments, the pre-determined period of time is about 75 seconds.

This disclosure provides, in another aspect, a method for forming gas-filled microspheres comprising identifying a vial comprising an ultrasound contrast agent formulation requiring activation for a pre-determined first period of time using a shaking device capable of selecting the first period of time from two pre-determined periods of time, based on the identity of the vial.

In some embodiments of any of the foregoing aspects and embodiments, the method is automated.

In some embodiments of any of the foregoing aspects and embodiments, the two pre-determined periods of time are about 45 seconds and about 75 seconds.

In some embodiments of any of the foregoing aspects and embodiments, the method produces substantially similar gas-filled microspheres from a first vial and a second vial provided the first vial is shaken for a first period of time and the second vial is shaken for a second different period of time.

This disclosure provides, in another aspect, a method for imaging a subject comprising administering to a subject in need thereof gas-filled microspheres prepared according to any one of the foregoing claims, and obtaining one or more images of the subject using ultrasound.

This disclosure provides, in another aspect, a device capable of being used in the formation of gas-filled microspheres in accordance with any one of the foregoing methods. In some embodiments, the device further comprises a counter that counts a number of times the device has been used, a number of times the device has shaken for a first period of time, and/or a number of times the device has shaken for a second period of time.

This disclosure provides, in another aspect, a device that activates a UCA formulation and that distinguishes an aqueous UCA formulation from a non-aqueous UCA formulation. In some embodiments, the device activates an aqueous UCA formulation for a shorter period of time than a non-aqueous UCA formulation.

This disclosure provides, in another aspect, a shaking device comprising a holder, means for shaking the holder, wherein the holder shakes a vial comprising a UCA formulation for different pre-determined periods of time.

In some embodiments, the device further comprises means for automatically identifying the pre-determined period of time the vial must be shaken to form gas-filled microspheres.

In some embodiments, the shaking device imparts a reciprocating motion to the vial when present in the holder.

In some embodiments, the first pre-determined period of time is about 45 seconds. In some embodiments, the second pre-determined period of time is about 75 seconds.

In some embodiments, the means for identifying the vial comprises an RFID reader which responds to a first RFID label by shaking the vial for a first period of time, and which responds to a second RFID label by shaking the vial for a second period of time, wherein the first and second periods of time are different. In some embodiments, the means for identifying the vial comprises a microchip reader which responds to a first microchip by shaking the vial for a first period of time, and which responds to a second microchip by shaking the vial for a second period of time. In some embodiments, the means for identifying the vial comprises a barcode scanner which responds to a first barcode by shaking the vial for a first period of time, and which responds to a second barcode by shaking the vial for a second period of time. In some embodiments, the RFID label, the microchip or the barcode is present on the vial.

In some embodiments, the UCA formulation is a non-aqueous UCA formulation.

This disclosure provides, in another aspect, a shaking device for forming gas-filled microspheres comprising an identification means capable of identifying and distinguishing between a first vial and a second vial, each vial comprising a UCA formulation, and an automated shaking means capable of shaking for only one of at least two different pre-determined periods of time based on the identification of the vial.

In some embodiments, the at least two different pre-determined periods of time are about 45 seconds and about 75 seconds.

In some embodiments, the identification means comprises an RFID reader, a microchip reader, or a barcode scanner.

This disclosure provides, in another aspect, a shaking device for forming gas-filled microspheres comprising a holder capable of identifying and distinguishing between a first vial and a second vial, each vial comprising a UCA formulation, and automated means for shaking a vial in the holder for one of two pre-determined periods of time based on whether a first vial or a second vial is identified.

In some embodiments of any of the foregoing aspects and embodiments, the shaking device imparts a reciprocating motion to a vial when present in the holder.

In some embodiments, the first pre-determined period of time is about 45 seconds. In some embodiments, the second pre-determined period of time is about 75 seconds.

In some embodiments, the holder comprises an RFID reader.

In some embodiments, the holder assumes a first configuration if the first vial is present and a second configuration if a second vial is present, and wherein the first configuration indicates presence of the first vial and the second configuration indicates presence of the second vial.

In some embodiments, the device further comprises a counter that counts a number of times the shaking device has been used, a number of times the shaking device has shaken for a first period of time, and/or a number of times the shaking device has shaken for a second period of time.

This disclosure provides, in another aspect, a shaking device comprising a holder capable of identifying a vial comprising a UCA formulation, and means for shaking the holder, wherein the holder is capable of shaking only for a pre-determined period of time to form gas-filled microspheres, based on the vial identity.

This disclosure provides, in another aspect, a shaking device comprising a holder, means for shaking the holder, wherein the holder is capable of shaking only for a pre-determined period of time, and means for identifying a vial comprising a UCA formulation when present in the holder and then shaking the identified vial for the pre-determined period of time to form gas-filled microspheres, wherein the means for identifying the vial comprises an RFID reader, a microchip reader, or a barcode scanner.

This disclosure provides, in another aspect, a kit comprising any of the foregoing shaking devices, with instructions for activation of a UCA formulation. In some embodiments, the kit further comprises a container, such as a vial, comprising the UCA formulation. In some embodiments, the UCA formulation is a non-aqueous UCA formulation.

In some embodiments, the kit further comprises the first vial or the second vial, each vial comprising a UCA formulation.

This disclosure provides, in another aspect, a non-transitory computer readable medium programmed with a plurality of instructions that, when executed by at least one processor of a shaking device perform a method, the method comprising: determining based, at least in part, on an identification of a sample type in a vial comprising a UCA formulation inserted into a holder of the shaking device at least one action to perform; and instructing the shaking device to perform the determined at least one action based, at least in part, on the identification.

This disclosure provides, in another aspect, a shaking device comprising: a holder configured to identify a type of sample in a vial comprising a UCA formulation inserted into the holder; at least one storage device configured to store at least one data structure identifying one or more actions to perform for each of a plurality of sample types;

at least one processor programmed to access the at least one data structure to determine the one or more actions to perform on the vial based on the identified sample type; and at least one component configured to perform the one or more actions determined by the at least one processor.

These and other aspects and embodiments of the invention will be described in greater detail herein.

BRIEF DESCRIPTION OF THE DRAWINGS

Various embodiments will now be described, by way of example, with reference to the accompanying drawings, in which.

DETAILED DESCRIPTION

Figure 1:
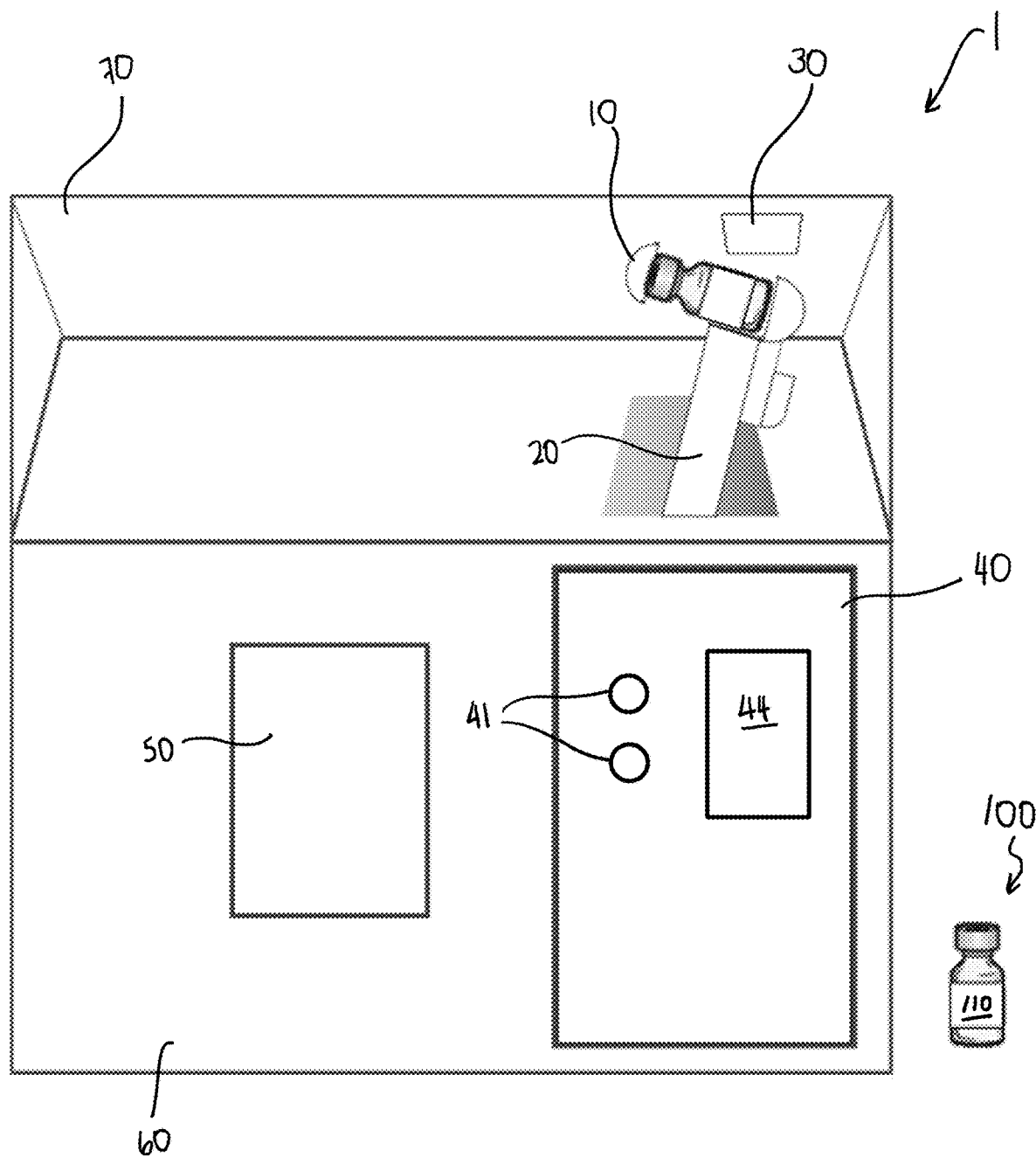
FIG. 1 is a schematic of a sample handling device and sample vial according to one aspect.

Provided herein are new and improved UCA formulations having one or more advantages over previously developed UCA formulations. One such improved UCA formulation is a non-aqueous UCA formulation comprising lipids and a perfluorocarbon gas in a non-aqueous solution. Another such improved UCA formulation is an aqueous UCA formulation comprising lipids and a perfluorocarbon gas in an aqueous solution. Each of these UCA formulations provide specific advantages over existing UCA formulations including for example stability at elevated temperatures (e.g., room temperature) or enhanced safety profiles.

Some of these new formulations however have specific activation requirements, some of which are markedly different from the activation requirements of existing formulations. For example, it has been found that the non-aqueous UCA formulations described herein must be activated for longer periods of time than an existing UCA formulation even though both can be activated using the same device. This can present a challenge to ensure that each UCA formulation is activated for its specific required time.

Provided herein are methods and means (e.g., devices) for facilitating proper and accurate preparation of activation-dependent UCA. These methods and means reduce the risk of improper preparation of such UCA. UCAs that are not properly and accurately prepared have too few gas-filled microspheres, thereby reducing signal obtainable from such UCAs, at best. At worst, UCAs that are not properly and accurately prepared could cause tissue ischemia by occluding capillary beds, and even patient death. Thus, it is imperative that activation-dependent UCAs are properly handled and prepared. This disclosure provides methods and means including devices that simplify the accurate preparation of activation-dependent UCAs. Unless otherwise stated, the UCA of this disclosure are activation-dependent UCA, and thus the terms "UCA" and "activation-dependent UCA" are used interchangeably.

With the development of new and improved non-aqueous UCA formulations that require different activation times or in some instances different activation rates (or shaking rates), robust, consistent and error-free product differentiation is required. The methods and means (e.g., devices) provided herein share the unique feature of distinguishing between different activation-dependent UCA formulations. As will be described in greater detail below, each activation-dependent UCA formulation will have its own specific activation criteria (or parameters) and therefore each such UCA formulation must be activated in only a certain manner. The methods and means (e.g., devices) provided herein commonly identify and thus distinguish an activation-dependent UCA formulation from other activation-dependent UCA formulations and activate the identified UCA formulation accordingly. This ensures that activation-dependent UCA formulations are activated for their specific pre-determined and prescribed periods of time, in some instances using specific shaking parameters. In some embodiments, the methods are performed and the means (e.g., devices) operated in relatively autonomous manner such that there is little risk of end user error in the activation process.

An FDA-approved activation-dependent UCA formulation is DEFINITY®. As described in greater detail below, DEFINITY® is provided in a vial as an aqueous suspension of lipids with a perflutren gas headspace. When activated for its prescribed period of time of 45 seconds using a VIAL-MIX® (or VIALMIX® device, as the terms are used interchangeably), "activated DEFINITY®" comprises a maximum of $1.2 \times 10^{10}$ perflutren lipid microspheres per ml of suspension. Activation for the wrong duration or shake speed will impact the microsphere profile, and render the UCA suboptimal or unusable in some instances. With the advent of at least one additional activation-dependent UCA formulation, in the form of a non-aqueous activation-dependent UCA formulation described below, it is important to ensure there is no confusion between different activation-dependent UCA formulations and that each is handled and activated properly, given the adverse consequences that can otherwise ensue.

Also provided herein are improved means (e.g., devices) for activating a UCA formulation. As an example, certain improved devices may comprise counters that can monitor use of the device, including lifetime use of the device, that can be useful in avoiding mechanical malfunction at critical times. They may also comprise temperature sensors that can measure the temperature of a container prior to activation. As described in greater detail herein, some of these devices may also be able to activate more than one UCA formulation, and may therefore be capable of identifying and optionally distinguishing between two or more UCA formulations. In this latter respect, the device may automatically recognize a container comprising a UCA formulation and based on such identity, which may be imparted for example by the label, shape, color or size of the container, or the optical properties of its contents, may activate the UCA formulation for a pre-determined period of time which in turn may be selected between two or more different pre-determined periods of time. The device may be able to perform such recognition with no or minimal user input.

Activation-Dependent UCAs

As used herein, a UCA refers to gas-filled microspheres that are useful in enhancing ultrasound signal. In most instances, the UCA is provided in solution such as a pharmaceutically acceptable solution. Depending on the concentration of microspheres in the UCA, it may be diluted with a pharmaceutically acceptable carrier prior to administration to a subject, although this may not be required in some instances.

An activation-dependent UCA formulation, as used herein, refers to a composition that must be activated in order to form gas-filled microspheres. A UCA formulation typically contains no such gas-filled microspheres (or such a low concentration of them to not be clinically useful), and must be activated in order to form microspheres of sufficient diameter and concentration to be clinically useful.

Activation-dependent UCA formulations typically require vigorous shaking prior to use to form gas-filled microspheres. Such activation is performed by an end user or an intermediate, but not the supplier or manufacturer of the UCA formulation. Activation-dependent UCA formulations are typically packaged in vials that minimally house a lipid solution and a gas. The shaking of the lipid solution and the gas results in the formation of gas-filled microspheres that act as the contrast agent in an ultrasound imaging procedure.

Unless otherwise stated, the UCA formulations of this disclosure are activation-dependent UCA formulations, and thus the terms "UCA formulation" and "activation-dependent UCA formulation" are used interchangeably.

By "gas-filled", as used herein, it is meant the microspheres comprise gas, such as a perfluorocarbon gas including but not limited to perflutren gas, in their internal cavity.

The lipid shell that encapsulates the gas may be arranged as a unilayer or a bilayer, including unilamellar or multilamellar bilayers. The microspheres may have a mean diameter of less than 10 microns, or less than 6 microns, or less than 3 microns, or more preferably less than 2 microns. These mean diameters intend that, when a population of microspheres is analyzed, the mean diameter of the population is less than 10 microns, or less than 6 microns, or less than 3 microns, or more preferably less than 2 microns. The microspheres may have a mean diameter in the range of 0.5 to 3 microns, or 1 to 2 microns, or 1.4 to 1.8 microns, or 1.4 to 1.6 microns. The mean diameter may be about 1.6 microns.

Prior to use, an activation-dependent UCA formulation must be shaken vigorously, to form gas-filled microspheres. In some instances, the microspheres may be combined with, for example, an aqueous solution prior to withdrawal from their container. This is particularly the case with microspheres made from non-aqueous UCA formulations. Such a step is referred to as reconstitution, in the context of this disclosure. In some instances, the microspheres, whether or not reconstituted, may be withdrawn from their container and combined in another solution, such as an aqueous solution, prior to administration to a subject. Such a step is referred to as dilution, in the context of this disclosure. The reconstituted population of microspheres may be used neat or after dilution in a pharmaceutically acceptable solution. Such dilution may be about 10-fold up to and about 50-fold, although it is not so limited.

As used herein, gas-filled microspheres and lipid-encapsulated gas microspheres are used interchangeably.

UCA formulations minimally comprise one or more lipid types and a gas such as perfluorocarbon gas such as perflutren gas. As described in greater detail herein, UCA formulations include aqueous UCA formulations such as DEFINITY® and non-aqueous UCA formulations such as DEFINITY-II. DEFINITY® comprises lipids DPPA, DPPC and MPEG5000-DPPE, propylene glycol and glycerol in an aqueous solution together with perflutren gas. DEFINITY-II, on the other hand, comprises lipids DPPA, DPPC and MPEG5000-DPPE, and propylene glycol and glycerol together with a perfluorocarbon gas (e.g., perflutren gas).

DEFINITY®

DEFINITY® is an example of an aqueous UCA formulation. Activated DEFINITY® is approved by the FDA for use in subjects with suboptimal echocardiograms to opacify the left ventricular chamber and to improve the delineation of the left ventricular endocardial border. DEFINITY® is provided in a vial comprising a single phase solution comprising DPPA, DPPC and MPEG5000-DPPE in a 10:82:8 mole % ratio in an aqueous solution, and a headspace comprising perfluoropropane gas. Prior to its administration to a subject, DEFINITY® is activated by vigorous shaking, such as vigorous mechanical shaking, and is thereafter referred to as "activated DEFINITY®". Activation results in the formation of a sufficient number of lipid-encapsulated gas microspheres having an average diameter of 1.1 to 3.3 microns. DEFINITY® however must be refrigerated until just prior to use. This limits its utility particularly in settings that lack appropriate refrigeration, particularly during the storage period.

In other aqueous UCA formulations, DPPA, DPPC and DPPE may be used in molar percentages of about 77-90 mole % DPPC, about 5-15 mole % DPPA, and about 5-15 mole % DPPE, including DPPE-MPEG5000. Preferred ratios of each lipid include weight % ratios of 6.0 to 53.5 to 40.5 (DPPA:DPPC:MPEG5000-DPPE) or a mole % ratio of 10 to 82 to 8 (10:82:8) (DPPA:DPPC:MPEG5000-DPPE).

DEFINITY-II and Other Non-Aqueous UCA Formulations

Contemplated herein are a variety of non-aqueous UCA formulations. Some such formulations comprise a non-aqueous mixture of one or more lipids and propylene glycol (PG), or glycerol (G), or propylene glycol and glycerol (PG/G). These formulations may be stored at higher temperatures (e.g., room temperature) for longer periods of time than were previously thought possible, without significant degradation. The non-aqueous UCA formulations, for example DEFINITY-II, may comprise less than 10%, less than 5%, or less than 2% impurities when stored at room temperature for a period of time, including for example, about 1 month, about 2 months, about 3 months, about 6 months, or longer including about 1 year, or about 2 years. Significantly, the non-aqueous UCA formulations may comprise fewer impurities than DEFINITY® when both formulations are stored at room temperature (i.e., when the non-aqueous UCA formulation and DEFINITY® formulation are stored at room temperature). This reduction in impurity level may be a difference of about 1%, about 2%, about 3%, about 4%, or about 5%, or more.

The non-aqueous mixture of lipids in propylene glycol, or glycerol, or propylene glycol and glycerol may be a mixture having less than or equal to 5% water by weight (i.e., weight of water to the weight of the combination of lipids and propylene glycol and/or glycerol). In some instances, the non-aqueous mixture comprises less than 5% water (w/w), 1-4% water (w/w), 1-3% water (w/w), 2-3% water (w/w), or 1-2% water (w/w). In some instances, the non-aqueous mixture comprises less than 1% water (w/w). The water content may be measured at the end of manufacture (and prior to long term storage) or it may be measured after storage, including long term storage, and just before use.

The non-aqueous mixture also may be salt-free intending that it does not contain any salts other than lipid counter-ions. More specifically, and as an example, lipids such as DPPA and DPPE are typically provided as sodium salts. As used herein, a salt-free non-aqueous mixture may comprise such counter-ions (e.g., sodium if DPPA and/or DPPE are used) but they do not contain other ions. In some instances, the non-aqueous mixture is free of sodium chloride or chloride.

The non-aqueous mixture may comprise a buffer. The buffer may be an acetate buffer, a benzoate buffer, or a salicylate buffer, although it is not so limited. Non-phosphate buffers are preferred in some instances due to their dissolution profiles in the non-aqueous mixtures provided herein. In some instances, a phosphate buffer may be used (e.g., following or concurrent with addition of aqueous diluent such as the reconstitution or dilution step, as discussed earlier).

In some embodiments, the non-aqueous mixture comprises, consists of, or consists essentially of (a) one or more lipids, (b) propylene glycol, or glycerol, or propylene glycol/ glycerol, and (c) a non-phosphate buffer. Such non-aqueous mixtures may be provided together with a gas such as a perfluorocarbon gas or they may be provided alone (i.e., in the absence of a gas). Such non-aqueous mixtures may be provided in single use amounts and/or in single use containers, with or without a gas. Such containers will typically be sterile.

The non-phosphate buffer may be, but is not limited to, an acetate buffer, a benzoate buffer, a salicylate buffer, a diethanolamine buffer, a triethanolamine buffer, a borate buffer, a carbonate buffer, a glutamate buffer, a succinate buffer, a malate buffer, a tartrate buffer, a glutarate buffer, an aconite buffer, a citrate buffer, a lactate buffer, a glycerate buffer, a gluconate buffer, and a tris buffer. It is within the skill of the ordinary artisan to determine and optimize the concentration of buffer for each buffer type.

DPPA, DPPC and DPPE may be used in molar percentages of about 77-90 mole % DPPC, about 5-15 mole % DPPA, and about 5-15 mole % DPPE, including DPPE-PEG5000. Preferred ratios of each lipid include weight % ratios of 6.0 to 53.5 to 40.5 (DPPA:DPPC:MPEG5000-DPPE) or a mole % ratio of 10 to 82 to 8 (10:82:8) (DPPA:DPPC:MPEG5000-DPPE).

In some instances, the lipid concentration may range from about 0.1 mg to about 20 mg per mL of non-aqueous mixture, including about 0.9 mg to about 10 mg per mL of non-aqueous mixture and about 0.9 mg to about 7.5 mg per mL of non-aqueous mixture. In some embodiments, the lipid concentration may range from about 0.94 mg to about 7.5 mg lipid per mL of non-aqueous mixture, including about 1.875 mg to about 7.5 mg lipid per mL of non-aqueous mixture, or about 3.75 mg to about 7.5 mg lipid per mL of non-aqueous mixture. In some instances, the lipid concentration is about 0.94 mg to about 1.875 mg per mL of non-aqueous mixture, about 1.875 mg to about 3.75 mg per mL of non-aqueous mixture, or about 3.75 mg to about 7.5 mg of total lipid per mL of non-aqueous mixture.

As an example, the lipid concentration may range from about 0.1 mg to about 10 mg lipid per mL of propylene glycol/glycerol (combined), including about 1 mg to about 5 mg lipid per mL of propylene glycol/glycerol (combined). In some instances, the lipid concentration is about 0.94 mg to about 3.75 mg lipid per mL of propylene glycol/glycerol (combined).

As another example, the lipid concentration may range from about 0.1 mg to about 20 mg lipid per mL of propylene glycol, including about 1 mg to about 10 mg lipid per mL of propylene glycol, or about 2 mg to about 7.5 mg lipid per mL of propylene glycol, or about 3.75 mg to about 7.5 mg lipid per ml of propylene glycol. In some embodiments, the lipid concentration is about 1.875 mg to about 7.5 mg lipid per mL of propylene glycol, including about 3.75 mg to about 7.5 mg lipid per mL of propylene glycol.

As yet another example, the lipid concentration may range from about 0.1 mg to about 20 mg lipid per mL of glycerol, including about 1 mg to about 10 mg lipid per mL glycerol, or about 2 mg to about 7.5 mg lipid per mL of glycerol, or about 3.75 mg to about 7.5 mg lipid per ml of glycerol. In some instances, the lipid concentration is about 1.875 mg to about 7.5 mg lipid per mL of glycerol, including about 3.75 mg to about 7.5 mg lipid per mL of glycerol.

DEFINITY-II comprises lipids DPPA, DPPC and MPEG5000-DPPE at a mole % ratio of 10 to 82 to 8 (10:82:8) and a total lipid content of 3.75 mg/mL, and propylene glycol (517.5 mg/mL), glycerol (631 mg/mL), Sodium acetate (0.370 mg/mL), Acetic acid (0.030 mg/mL) together with a perfluoropropane (Perflutren) gas headspace (6.52 mg/mL).

The microspheres may be reconstituted or diluted in an aqueous diluent, and such aqueous diluent may comprise salts such as but not limited to sodium chloride, and thus may be regarded as a saline solution. The aqueous diluent may comprise a buffer such as a phosphate buffer, and thus may be regarded as a buffered aqueous diluent. The aqueous diluent may be a buffered saline solution. The non-aqueous mixture may comprise a buffer such as a non-phosphate buffer, examples of which are provided herein. The non-aqueous mixture and the aqueous diluent may both comprise a buffer. In typical embodiments, either the non-aqueous mixture or the aqueous diluent comprises a buffer, but not both. The buffer concentration will vary depending on the type of buffer used, as will be understood and within the skill of the ordinary artisan to determine. The buffer concentration in the non-aqueous lipid formulation may range from about 1 mM to about 100 mM. In some instances, the buffer concentration may be about 1 mM to about 50 mM, or about 1 mM to about 20 mM, or about 1 mM to about 10 mM, or about 1 mM to about 5 mM, including about 5 mM.

The final formulation to be administered, typically intravenously, to a subject including a human subject may have a pH in the range of 4-8 or in a range of 4.5-7.5. In some instances, the pH may be in a range of about 6 to about 7.5, or in a range of 6.2 to about 6.8. In still other instances, the pH may be about 6.5 (e.g., 6.5+/−0.5 or +/−0.3). In some instances, the pH may be in a range of 5 to 6.5 or in a range of 5.2 to 6.3 or in a range of 5.5 to 6.1 or in a range of 5.6 to 6 or in a range of 5.65 to 5.95. In still another instance, the pH may be in a range of about 5.7 to about 5.9 (e.g., +/−0.1 or +/−0.2 or +/−0.3 either or both ends of the range). In another instance, the pH may be about 5.8 (e.g., 5.8+/−0.15 or 5.8+/−0.1).

In some embodiments, the aqueous diluent comprises glycerol, a buffer such as phosphate buffer, salt(s) and water. Such an aqueous diluent may be used with a non-aqueous mixture that lacks glycerol. In some embodiments, the lipid solution further comprises saline (salt(s) and water combined) and glycerol in a weight ratio of 8:1.

In some embodiments, the aqueous diluent comprises propylene glycol, a buffer such as phosphate buffer, salt(s) and water. Such an aqueous diluent may be used with a non-aqueous mixture that lacks propylene glycol.

In some embodiments, the aqueous diluent comprises a buffer such as phosphate buffer, salt(s) and water. Such an aqueous diluent may be used with a non-aqueous mixture that comprises both propylene glycol and glycerol.

The microspheres may be reconstituted and used directly (neat) or they may be reconstituted and diluted. Reconstitution and dilution involve combining the microspheres with an aqueous solution, such as a pharmaceutically acceptable solution. Either step or both together may yield microsphere concentrations of at least $1 \times 10^7$ microspheres per ml of solution, or at least $5 \times 10^7$ microspheres per ml of solution, or at least $7.5 \times 10^7$ microspheres per ml of solution, or at least $1 \times 10^8$ microspheres per ml of solution, or at least $1 \times 10^9$ microspheres per ml of solution, or about $5 \times 10^9$ microspheres per ml of solution. The range of microsphere concentration may be, in some instances, $1 \times 10^7$ to $1 \times 10^{10}$ microspheres per ml of solution, and more typically $5 \times 10^7$ to $5 \times 10^9$ microspheres per ml of solution. A reconstituted population of microspheres may be further diluted about 10-fold up to and about 50-fold, without limitation.

In some instances, activation of the non-aqueous UCA formulation followed by reconstitution yields about $4\text{-}5 \times 10^9$ microspheres per ml of solution, which may be diluted about 10 fold to yield about $4\text{-}5 \times 10^8$ microspheres per ml of solution.

DEFINITY-II is described in greater detail in PCT Application PCT/US2015/067615, the entire contents of which are incorporated by reference herein.

DEFINITY-II is contemplated for use in a manner identical to that of DEFINITY®. Thus, for example, DEFINITY-II may be used in subjects with suboptimal echocardiograms to opacify the left ventricular chamber and to improve the delineation of the left ventricular endocardial border, among other imaging applications.

Other Aqueous UCA Formulations

Other aqueous UCA formulations are now being developed. Some new aqueous UCA formulations comprise, relative to DEFINITY®, a smaller volume of aqueous lipid solution (i.e., the aqueous solution comprising lipids) and a larger gas headspace. Other new aqueous UCA formulations comprise, relative to DEFINITY®, a lower lipid concentration in the aqueous solution. And still other aqueous UCA formulations are provided in containers of various shape and size (and thus volume), relative to DEFINITY®. All of these new aqueous UCA formulations can be activated to yield gas-filled microspheres on par with activated DEFINITY®, including mean diameter profile, without compromising the acoustic properties of the microspheres. The ability to form lipid-encapsulated gas microspheres suitable for clinical use using substantially less lipid by reducing either the volume of lipid solution or the lipid concentration is beneficial for a number of reasons, including reducing material wastage and the likelihood of overdosing a subject. The choice of container would allow the end user to select the most convenient shape and size (volume) for their desired application.

An example of one such new aqueous UCA formulation, referred to herein as DEFINITY-III, comprises lipids DPPA, DPPC and PEG5000-DPPE (where PEG5000 includes without limitation hydroxy-PEG5000 or MPEG5000) in an aqueous solution together with a perfluorocarbon gas (e.g., perflutren gas) in a container, wherein the perfluorocarbon gas occupies about 60-85% of the container volume. DEFINITY®, in contrast, is provided in a container (i.e., a vial) wherein the perfluorocarbon gas (i.e., perflutren gas) occupies about 54% of the container volume.

Another example of new aqueous UCA formulation, referred to herein as DEFINITY-IV comprises an aqueous lipid solution comprising about 0.1 mg to about 0.6 mg of DPPA, DPPC and PEG5000-DPPE (combined) per ml of solution, and a perfluorocarbon gas, in a container.

These new aqueous UCA formulations including DEFINITY-III and DEFINITY-IV are described in greater detail in PCT Application PCT/US2014/063267, the entire contents of which are incorporated by reference herein.

Activation

UCA formulations are vigorously shaken to form gas-filled microspheres which will typically be used as UCA. Such gas-filled microspheres may be formed directly or they may be formed through a process that involves formation of microspheres and incorporation of gas into such microspheres. Activation is typically carried out by vigorously shaking of a container (e.g., a vial) comprising a UCA formulation. The UCA formulation minimally comprises lipids and gas, and thus activation minimally results in gas-filled lipid microspheres. The lipids may be present in an aqueous solution such as is the case with DEFINITY®, DEFINITY-III and DEFINITY-IV or they may be present in a non-aqueous solution such as is the case with novel UCA formulations including for example DEFINITY-II, described in greater detail herein. Thus, in some instances, activation comprises shaking an aqueous solution comprising a lipid in the presence of a gas, such as a perfluorocarbon gas (e.g., perflutren). In other instances, activation comprises shaking a non-aqueous solution comprising a lipid in the presence of a gas, a perfluorocarbon gas (e.g., perflutren). It is to be understood that perflutren, perflutren gas and octafluoropropane are used interchangeably herein.

Shaking, as used herein, refers to a motion that agitates a solution, whether aqueous or non-aqueous, such that gas is introduced from the local ambient environment within the container (e.g., vial) into the solution. Any type of motion that agitates the solution and results in the introduction of gas may be used for the shaking. The shaking must be of sufficient force or rate to allow the formation of foam after a period of time. Preferably, the shaking is of sufficient force or rate such that foam is formed within a short period of time, as prescribed by the particular UCA formulation. Thus in some instances such shaking occurs for about 30 seconds, or for about 45 seconds, or for about 60 seconds, or for about 75 seconds, or for about 90 seconds, or for about 120 seconds, including for example for 30 seconds, or for 45 seconds, or for 60 seconds, or for 75 seconds, or for 90 seconds, or for 120 seconds. In some instances, the activation may occur for a period of time in the range of 60-120 seconds, or in the range of 90-120 seconds.

The disclosure contemplates that, in some instances, the shaking time (or duration) will vary depending on the type of UCA formulation being activated. For example, in some instances, an aqueous UCA formulation may be shaken for shorter periods of time than a non-aqueous UCA formulation. The disclosure contemplates that, in such instances, the shaking rate (or shaking speed, as those terms are used interchangeably herein) may be constant. Thus an activation or shaking means such as an activation or shaking device may be set to shake at one rate (defined in terms of number of shaking motions per minute, for example) for two or more different pre-determined periods of time.

The disclosure further contemplates that, in some instances, the shaking rate will vary depending on the type of UCA formulation being activated. For example, in some instances, an aqueous UCA formulation may be shaken at a slower shaking rate than a non-aqueous UCA formulation. The disclosure contemplates that, in such instances, the shaking time (or duration, as those terms are used interchangeably herein) may be constant. Thus an activation or shaking means such as an activation or shaking device may be set to shake at two or more different pre-determined shaking rates (defined in terms of number of shaking motions per minute, for example) for one set period of time.

The disclosure further contemplates that, in some instances, the shaking time and the shaking rate will vary depending on the type of UCA formulation being activated. For example, in some instances, an aqueous UCA formulation may be shaken for a first period of time at a first shaking rate and a non-aqueous UCA formulation may be shaken for a second period of time at a second shaking rate, and the first and second periods of time may be different and the first and second shaking rates may be different. Thus an activation or shaking means such as an activation or shaking device may be set to shake at two or more different pre-determined shaking rates (defined in terms of number of shaking motions per minute, for example) for two or more different pre-determined periods of time. For example, an activation or shaking means such as an activation or shaking device may be set to shake at (1) a first pre-determined shaking rate for a first pre-determined period of time and (2) a second pre-determined shaking rate for a second pre-determined period of time, and the first and second periods of time are different and the first and second shaking rates are different. DEFINITY® activation requires vigorous shaking for about 45 seconds with a VIALMIX®. Unless indicated otherwise, the term "about" with respect to activation time intends a time that is +/−20% of the noted time (i.e., 45+/−9 seconds). DEFINITY-II may be activated with a VIALMIX® for periods of time ranging from 60 to 120 seconds. In some instances, DEFINITY-II is activated for about 75 seconds (i.e., 75+/−15 seconds). DEFINITY-II may be activated for longer periods of time including 90-120 seconds The shaking may be by swirling (such as by vortexing), side-to-side, or up and down motion. Further, different types of motion may be combined. The shaking may occur by shaking the container (e.g., the vial) holding the aqueous or non-aqueous lipid solution, or by shaking the aqueous or non-aqueous solution within the container (e.g., the vial) without shaking the container (e.g., the vial) itself. Shaking is carried out by machine in order to standardize the process. Mechanical shakers are known in the art and their shaking mechanisms or means may be used in the devices of the present disclosure. Examples include amalgamators such as those used for dental applications. Vigorous shaking encompasses at least 1000, at least 2000, at least 3000, at least 4000, at least 4500, at least 5000 or more shaking motions per minute. In some instances, vigorous shaking includes shaking in the range of 4000-4800 shaking motions per minute. VIALMIX® for example targets shaking for 4530 "figure of eight" revolutions per minute, and tolerates shaking rates in the range of 4077-4756 revolutions per minute. Vortexing encompasses at least 250, at least 500, at least 750, at least 1000 or more revolutions per minute. Vortexing at a rate of at least 1000 revolutions per minute is an example of vigorous shaking, and is more preferred in some instances. Vortexing at 1800 revolutions per minute is most preferred.

The shaking rate can influence the shaking duration needed. A faster shaking rate will tend to shorten the duration of shaking time needed to achieve optimal microbubble formation. For example, shaking at 4530 rpm for a 45 second duration will achieve 3398 total revolutions on a VIALMIX®. Shaking at 3000 rpm would require 68 seconds to achieve the same number of revolutions. It will also be understood, therefore, that a slower shaking rate will tend to lengthen the duration of shaking time needed to achieve optimal microbubble formation. The duration and shake speed required will also be influenced by the shape of the travel path and amplitude of shaking. The velocity the liquid in the container reaches and the forces exerted upon change of direction will influence gas incorporation. These aspects will be impacted upon based on the shaker arm length and path, the container shape and size, the fill volume and the formulation viscosity. Water has a viscosity of approximately 1.14 cps at 15° C. (Khattab, I. S. et al., Density, viscosity, surface tension, and molar volume of propylene glycol+water mixtures from 293 to 323 K and correlations by the Jouyban-Acree model Arabian Journal of Chemistry (2012). In contrast, propylene glycol has a viscosity of 42 cps at 25° C. (Khattab, I. S. et al., Density, viscosity, surface tension, and molar volume of propylene glycol+water mixtures from 293 to 323 K and correlations by the Jouyban-Acree model Arabian Journal of Chemistry (2012) and glycerol has a viscosity of 2200 cps at 15° C. (Secut J B, Oberstak H E Viscosity of Glycerol and Its Aqueous Solutions. Industrial and Engineering Chemistry 43. 9 2117-2120 1951). DEFINITY-II has a high viscosity of 1150 cps at 15° C. Since DEFINITY® is predominantly water it has a much lower viscosity than DEFINITY-II.

The formation of gas-filled microspheres upon activation can be detected by the presence of a foam on the top of the aqueous or non-aqueous solution and the solution becoming white.

Activation is carried out at a temperature below the gel state to liquid crystalline state phase transition temperature of the lipid employed. By "gel state to liquid crystalline state phase transition temperature", it is meant the temperature at which a lipid layer (such as a lipid monolayer or bilayer) will convert from a gel state to a liquid crystalline state. This transition is described for example in Chapman et al., J. Biol. Chem. 1974 249, 2512-2521. The gel state to liquid crystalline state phase transition temperatures of various lipids will be readily apparent to those skilled in the art and are described, for example, in Gregoriadis, ed., Liposome Technology, Vol. I, 1-18 (CRC Press, 1984) and Derek Marsh, CRC Handbook of Lipid Bilayers (CRC Press, Boca Raton, Fla. 1990), at p. 139. Vigorous shaking can cause heating of the formulation based on the shake speed, duration, shaker arm length and path, the container shape and size, the fill volume and the formulation viscosity.

It will be understood by one skilled in the art, in view of the present disclosure, that the lipid(s) or lipid microspheres may be manipulated prior to or subsequent to being subjected to the methods provided herein. For example, after the shaking is completed, the gas-filled microspheres may be extracted from their container (e.g., vial). Extraction may be accomplished by inserting a needle of a syringe or a needle-free spike (e.g., PINSYNC®) into the container, including into the foam if appropriate, and drawing a pre-determined amount of liquid into the barrel of the syringe by withdrawing the plunger or by adding an aqueous liquid, mixing and drawing a pre-determined amount of liquid into the barrel of the syringe by withdrawing the plunger. As another example, the gas-filled microspheres may be filtered to obtain microspheres of a substantially uniform size. The filtration assembly may contain more than one filter which may or may not be immediately adjacent to each other.

Methods

Accordingly, this disclosure provides various methods for forming gas-filled microspheres. In some instances, these methods minimally comprise activating an activation-dependent UCA formulation to form gas-filled microspheres. Activation may be performed using an activation means (e.g., a shaking device). Such means may be capable of activation alone or it may be capable of identification of a UCA formulation (or its container) and activation of such formulation. Thus, some methods comprise identifying a UCA formulation and then activating such UCA formulation based on its identity. A single means (e.g., device) may perform both the identification and activation steps. Alternatively, different means may be use to perform each step. In still another embodiment, a means may be used to activate the formulation.

In some instances, these methods comprise activating an activation-dependent UCA formulation to form gas-filled microspheres using means (e.g., a device) that identifies a non-aqueous UCA formulation. Identification of a non-aqueous UCA formulation may involve reading a label specific to a non-aqueous UCA formulation. The means may be set to hold and activate the non-aqueous UCA formulation for a pre-determined period of time. In some embodiments, such pre-determined period of time is about 75 seconds.

In other instances, these methods comprise activating an activation-dependent UCA formulation to form gas-filled microspheres using a means that distinguish a non-aqueous UCA formulation from an aqueous UCA formulation (or alternatively, a means that distinguish an aqueous UCA formulation from a non-aqueous UCA formulation).

An aqueous UCA formulation is an aqueous solution comprising one or more lipid(s) and a gas. Upon activation, the lipids and gas together form the gas-filled microspheres. Examples of an aqueous UCA formulation are DEFINITY®, DEFINITY-III, and DEFINITY-IV.

A non-aqueous UCA formulation is a non-aqueous solution comprising one or more lipid(s) and a gas. Upon activation, the lipids and gas together form the gas-filled microspheres although in this case the microspheres are surrounded by a non-aqueous solution. An example of a non-aqueous UCA formulation is a room temperature stable formulation referred to herein as DEFINITY-II. As described in greater detail herein, DEFINITY-II minimally comprises lipids DPPA, DPPC and PEG5000-DPPE in propylene glycol and glycerol, along with a buffer and octafluoropropane (perflutren) gas. PEG5000 refers to PEG having a molecular weight of 5000 Daltons. It may be hydroxy-PEG or methoxy-PEG. In some embodiments, DEFINITY-II comprises MPEG5000-DPPE Thus examples of non-aqueous UCA formulations comprise, for example, lipids DPPA, DPPC and MPEG5000-DPPE, propylene glycol, glycerol, a buffer, and octafluoropropane (perflutren) gas; or lipids DPPA, DPPC and MPEG5000-DPPE, propylene glycol, a buffer, and octafluoropropane (perflutren) gas; or lipids DPPA, DPPC and MPEG5000-DPPE, glycerol, a buffer, and octafluoropropane (perflutren) gas; or lipids DPPA, DPPC and MPEG5000-DPPE, propylene glycol, glycerol, and octafluoropropane (perflutren) gas. Once activated, the gas-filled microspheres similarly comprise a DPPA/DPPC/MPEG5000 DPPE lipid shell that encapsulates the perflutren gas. These microspheres however are diluted in an aqueous solution, such as an aqueous saline solution and then administered to a subject, either as a bolus or continuous infusion injection.

Significantly, it has been found that these aqueous and non-aqueous UCA formulations have different optimal activation times in order to obtain diagnostically suitable gas-filled microspheres. For example, in some instances in which the shaking rate is about 4530 shaking motions (e.g., figure of 8 motions) per minute and shaking is performed using a VIALMIX®, some aqueous UCA formulations, including DEFINITY®, are activated in about 45 seconds while the non-aqueous UCA formulation DEFINITY-II is activated in 60-120 seconds and in some instances in about 75 seconds in order to achieve a substantially similar microsphere profile with respect to size distribution. The methods provided herein therefore facilitate the differentiation of a non-aqueous UCA formulation from aqueous UCA formulations such as DEFINITY®.

Other methods provided herein comprise identifying a labeled vial comprising a UCA formulation requiring activation for a pre-determined period of time using a shaking device comprising a detector and set to the pre-determined period of time or capable of automatically selecting the pre-determined period of time based on the identity of the vial, and activating the UCA formulation to form gas-filled microspheres. The pre-determined period of time may be 45 seconds or it may be 75 seconds, although it is not so limited.

Other methods provided herein comprise differentiating between two or more aqueous UCA formulations (such as for example DEFINITY®, DEFINITY-III and DEFINITY-IV), which require different activation times and optionally different shaking rates. The two or more aqueous UCA formulations may be differentiated based on their fill volume (i.e., the amount of liquid in their respective containers), or based on container shape and size. Fill volumes may be assessed, for example, using optical approaches (e.g., measuring absorbance of light by the formulation at a particular position along the length of the container). Container shape and size may be assessed, for example, using the holder which holds the container. Once an aqueous UCA formulation is identified (through differentiation from other UCA), it may then be activated for its prescribed period of time and using its prescribed shaking rate. Where the methods involve differentiation between two more UCA formulations, the activation means (e.g., the shaking device) may be set to shake at a pre-determined period of time, or it may be set to shake for two or more different pre-determined periods of time and would therefore be capable of automatically selecting one such period of time. Such means may comprise a detector. Similar methods are provided for differentiating and optionally activating non-aqueous UCA formulations. Similar methods are provided for differentiating between aqueous and non-aqueous UCA formulations, and optionally activating one or both UCA formulations.

Other methods provided herein comprise identifying an aqueous UCA formulation requiring activation for a pre-determined period of time, using a device that distinguishes the aqueous UCA formulation from a non-aqueous UCA formulation, and activating the aqueous UCA formulation for the pre-determined period of time to form gas-filled microspheres.

Other methods provided herein comprise identifying a UCA formulation requiring activation for a pre-determined period of time, using a device that distinguishes a non-aqueous UCA formulation from an aqueous UCA formulation (or vice versa), and activating the UCA formulation for a pre-determined period of time to form gas-filled microspheres. The device may be set to activate for only one pre-determined period of time (e.g., about 45 seconds if an aqueous UCA or about 75 seconds if a non-aqueous UCA), or it may be set to activate for two or more different pre-determined periods of time (e.g., about 45 seconds and about 75 seconds). It is to be understood that where two or more pre-determined periods of time are contemplated, such periods of time are different from each other.

Still other methods are provided that comprise identifying a UCA formulation requiring activation for a pre-determined period of time, and activating the UCA formulation for the pre-determined period of time to form gas-filled microspheres. For example, the methods comprise identifying a non-aqueous UCA formulation requiring activation for a pre-determined period of time, and activating the non-aqueous UCA formulation for the pre-determined period of time to form gas-filled microspheres. The UCA formulation may be identified and activated using a shaking device set to the pre-determined period of time or capable of automatically selecting the pre-determined period of time based on the identity of the UCA formulation.

Thus, in some instances, the methods comprise identifying a UCA formulation requiring activation for a pre-determined period of time, and activating the UCA formulation for the pre-determined period of time to form gas-filled microspheres using a shaking device that is set to two or more pre-determined periods of time or capable of automatically selecting between two pre-determined periods of time based on the identity of the UCA formulation. In some instances, the identity of the UCA formulation is provided by a label or tag on the container (e.g., vial) housing the formulation. In some instances, the identity of the UCA formulation is provided by the formulation itself or its volume, as described herein in more detail. The UCA formulation may be an aqueous UCA formulation or it may be a non-aqueous UCA formulation. The pre-determined period of time may be about 45 seconds. The pre-determined period of time may be in the range of 60-120 seconds or about 75 seconds.

Alternatively, other methods provided herein comprise identifying a labeled vial comprising a UCA formulation requiring activation for a fixed period of time and a pre-determined shake speed using a shaking device comprising a scanner set to the fixed period of time and pre-determined shake speed or capable of automatically selecting the pre-determined shake speed based on the identity of the vial, and activating the UCA formulation to form gas-filled microspheres. The pre-determined shake speed may be about 4530 rpm.

Still other methods comprise activating a UCA formulation using a shaking device that identifies the UCA formulation and automatically selects an activation time or shake speed (or shake rate, and the terms are used interchangeably herein) or both based thereon, wherein the UCA formulation is identified based on a unique identifier other than shape or size of a vial housing the UCA formulation.

Other methods comprise activating a first UCA formulation using a shaking device that can distinguish a first vial comprising the first UCA formulation from a second vial comprising a second UCA formulation.

Yet other methods comprise identifying a labeled vial comprising an aqueous UCA formulation requiring activation for a pre-determined first period of time, using a shaking device comprising a scanner and set to the pre-determined period of time or capable of automatically selecting the first pre-determined period of time from two pre-determined periods of time, based on the identity of the vial, and activating the UCA formulation to form gas-filled microspheres.

All of these methods may be automated in whole or in part. In some instances, the devices first identify the vial containing the UCA formulation and provide a prompt to the user to confirm the identification. In other instances, the devices identify and activate without any user input.

Devices

Identification of a UCA formulation and/or distinction between different UCA formulations can be achieved in a number of ways. For example, devices may be used with scanners able to read labels on the UCA formulation container (e.g., vial). In other instances, identification and/or distinction between different UCA formulations can be achieved using devices that recognize the shape and size of a container housing an aqueous UCA formulation versus a container housing a non-aqueous UCA formulation. These latter devices may comprise a single holder or they may comprise two or more holders. If a single holder, the holder may be capable of holding a container (e.g., a vial) housing a non-aqueous UCA formulation and incapable of holding a container (e.g., vial) housing an aqueous UCA formulation. Alternatively, the holder may be capable of holding a container (e.g., a vial) housing an aqueous UCA formulation and incapable of holding a container (e.g., vial) housing a non-aqueous UCA formulation.

According to one aspect, a device receives a container holding a UCA formulation, detects the UCA formulation type and performs different actions depending on the type of UCA formulation that is detected. The device associates certain actions with each UCA formulation type. After detecting a certain UCA formulation type, the device automatically performs the actions associated with that UCA formulation type.

A variety of different actions can be performed based on the UCA formulation type that is detected. In some embodiments, the device shakes the sample. In some embodiments, the device performs a specific shaking duration, pattern, and/or rate depending on the sample type that is detected. Examples of different shaking patterns include but are not limited to: side to side reciprocation, up and down reciprocation, vibration, a spinning motion, a figure-eight path, a circular path and back-and-forth tilting (e.g. rotating the container by some angle and reversing the action). For example, in one illustrative embodiment, the device associates a shaking duration of about 45 seconds with sample type "A" and about 75 seconds with sample type "B." When the device detects a sample type "A," the device automatically shakes the sample for about 45 seconds without requiring the user to input a shaking time. When the device detects a sample type "B," the device automatically shakes the sample for about 75 seconds.

Thus, this disclosure further contemplates devices that are capable of varying one or more parameters upon identification (and thus differentiation) of sample types. As an example, one device may shake with the same pattern and at the same shaking rate for all sample types, but may shake different sample types for different durations (i.e., different shaking times). As another example, one device may shake with the same pattern and for the same time for all sample types, but may shake different sample types at different rates (i.e., different shaking rates). As yet another example, one device may shake with the same shaking rate and for the same time for all sample types, but may shake different sample types with different shaking patterns. Alternatively, the device may respond to each sample type identified by setting, including potentially altering, two parameters, such as shaking rate and shaking time, or shaking rate and shaking pattern, or shaking time and shaking pattern. In still another embodiment, the device may respond to each sample identified by setting, including potentially altering, all three of these parameters (i.e., shaking rate, shaking time, and shaking pattern).

It should be appreciated that many other actions can be associated with a sample type. Examples of different actions that a device can perform in reaction to a detected sample type include but are not limited to: adjusting temperature settings, adjusting humidity settings, adjusting light settings (e.g. subjecting the sample to different intensities and/or frequencies of light), and/or inputting different substances into the container (e.g. reagents, dyes or other suitable additives).

Indicators

In some embodiments, the container holding the sample includes an indicator that indicates the sample type and the device include a detector that reads the indicator to detect the sample type. The indicator may be one that is machine- or device readable. Examples of machine- or device-readable indicators include magnetic stripes, chips/microchips, barcodes including linear, matrix and 2D barcodes, radio frequency identification (RFID) tags, color labels that are identifiable by color detection, and the like. Barcodes such as linear barcodes may be those that comply with or meet Uniform Code Council standards or Health Industry Business Communications Council standards. Such indicators may in turn be read, for example, from a device such as a magnetic stripe reader, a chip reader, a barcode scanner or reader, an RFID tag reader, and the like. Virtually any labeling technology that has been used for authentication and/or "track and trace" purposes may be used in conjunction with the containers provided herein.

The indicator may be positioned on any suitable portion of the sample container, such as the body of the container or the cap. In some embodiments, the indicator is integrally formed with or otherwise a part of the sample container. For example, the indicator may be a colored cap or a physical feature such as a protrusion or an indentation on the sample container. In other embodiments, the indicator is attached to the container via, for example, adhesive, magnets, hook-and-loop type fasteners, mechanical arrangement such as sliding the indicator behind holding tabs, or any other suitable attachment arrangement.

The indicator may provide the end user or an intermediate handler of the container a variety of information including but not limited to source and/or producer of the formulation contained therein, including for example the name of the company or company subsidiary that made the formulation and/or that produced components of the formulation, the date on which the formulation was made, the physical location where the formulation was made, the date of shipment of the container, the treatment of the container including for example whether it was stored in a remote location and the conditions and length of such storage, the date on which the container was delivered, the means of delivery, the National Drug Code (NDC) as prescribed by the FDA, content of the container, dose and method of use including route of administration, etc.

The indicator may serve one or more purposes including for example authentication of the container and the formulation contained therein. Authentication means the ability to identify or mark the container as originating and having been made by an authorized party, and it allows an end user or other party to identify container and formulations originating from another, unauthorized party. The indicator may also be used to track and trace a container. This feature can be used to follow a container and the formulation contained therein following production and up to the point of administration to a subject. In this regard, the movement of the container during that period of time may be stored in a database, and optionally such a database may be accessible to an end user to ensure the integrity of the formulation.

The indicator may also be a combined indicator, intending that it may contain information that is read using two different modes. For example, the indicator may contain information that is apparent and understandable to the visible eye (e.g., it may recite the name of the producer in words) and other information that is machine-readable, such as RFID embedded or barcode embedded information.

The indicator may also be a dual use indicator, intending that it may serve two or more purposes. For example, the indicator may contain information that identifies the formulation and further information that identifies the manufacturer and/or date of manufacture. This information may be conveyed in the same format or using different format (e.g., one may be provided in an RFID indicator and the other may be provided in a barcode label).

The label may also be capable of having information recorded on it (e.g. using RFID technology) by the device used to shake the vial. For example such information may be used to prevent re-activation of the vial by any appropriately equipped device if it has previously been shaken and is now beyond the expiry period for re-activation of previously-activated vials. The indicator may provide content that is visible and understandable to a human, such as for example the name of the manufacturer. Alternatively or additionally, the indicator may contain information that while readily visible to the human eye nevertheless provides no meaningful information in the absence of a lookup table or other form of database to which reference must be made. Such information for example may be provided as alpha-numeric code.

In some embodiments, the UCA formulation is in a container, such as a vial, and such container is labeled. The container may have an indicator in the form of a label that is affixed to one or more of its outer surfaces. In some embodiments, the indicator is a paper label or other such label that is visible by eye and capable of being read and understood by an end user without further aid or device. Alternatively, as discussed above, the indicator is one that is machine- or device readable.

Detectors

The device may include any suitable detector for reading the indicator. In some embodiments, the detector may operate via visual, photographic, imaging, electromagnetic, visible light, infrared and/or ultraviolet modalities.

For example, in some embodiments, the indicator is a barcode and the detector is a barcode scanner. In some embodiments, the indicator is an RFID tag and the detector is an RFID reader. In some embodiments, the indicator is a colored label and the detector is a color detecting scanner. In some embodiments, the indicator is a chip/microchip and the detector is a chip/microchip reader.

In some embodiments, the sample containers include an indexing feature that ensures that the indicator on the container is properly aligned with the detector on the device. Examples of indexing features include physical recesses or protrusions on the container cap or body that align with corresponding features on the holder such that the container can only fit into the holder in one orientation.

In some embodiments, the indicator is a physical component, such as a protrusion or an indentation on the container. The detector is a button on the device that is pushed or a sensor that is otherwise activated due to physical interaction with the physical component. In one illustrative embodiment, the indicator is a specifically shaped protruding tab on the cap of the sample container, and the device includes corresponding slots into which the tabs can be inserted. Each sample type is associated with a specific tab shape, and each tab shape exclusively fits with only one of the slots on the device. An L-shaped tab is associated with sample type "A," and an oval-shaped tab is associated with sample type "B." The portion of the device that interacts with the container cap has associated slots; one that receives the L-shaped tab and one that receives the oval-shaped tab. When an L-shaped tab is inserted into the holder, the tab presses a button within the L-shaped slot, and the device knows a sample type "A" has been received. When an oval-shaped tab is inserted into the holder, the tab presses a button within the oval-shaped slot, and the device knows a sample type "B" has been received.

In some embodiments, the device is able to detect the sample type based on one or more properties of the sample container. Examples of properties include weight, optical properties, and size of the container. Regarding weight, the weight of the sample may reflect a sample type. For example, containers having samples of type A may have one weight range and containers having samples of type B may have a second, different weight range. The device may include a scale or other weight detection apparatus that determines the combined weight of the container and sample. If the weight falls within the first range, the device determines that the sample is type A and if the weight falls within the second range, the device determines that the sample is type B. The weight detection apparatus may be integrated into the holder or may be a separate weighing station on the device. In the case of a separate weighing station, the user places the container in/on the weight detection apparatus, the device measures the weight to detect the sample type, and then the user or the device itself moves the sample container to the holder.

Regarding optical properties, each sample type may be associated with a known optical property. Examples of optical properties include but are not limited to index of refraction, absorption and fluorescence. The device may include a suitable instrument for measuring the optical property and, from the measurement, determine the associated sample type.

Regarding sample container size, each sample type may be associated with a different sized container. For example, sample type "A" may have a container that is larger than the container used for sample type "B." The device may detect container size in variety of ways. In some embodiments, the device has more than one holder—each holder being sized to accommodate one of the sample container sizes. Each sample container size may only fit into one of the holders. The device detects when and which holder has received a container. By knowing which holder has a container, the device determines the sample container size and the sample type associated with that container size. In another embodiment, the device has a single holder that can accommodate differently-sized containers. For example, the holder may have a spring-biased end that can be moved to different positions to accommodate larger containers. The device may have buttons or other sensors that detect the receipt of a container and the size at which the holder has been enlarged to in order to determine the container size. As another example, the user may need to manually adjust the holder size by removing filler pieces, flipping open doors, or otherwise moving components to size the holder to appropriately and snugly accommodate the sample container. The device would then sense the size of the holder and determine the container size accordingly. In other embodiments, the device may include visual detectors such as a camera and/or a laser to detect the size of the container. For example, a camera may take an image of the container and process the image to determine the size of the container. As another example, a laser may be directed to a position that would hit the container if a large-sized container is used but pass through nothing if a small-sized container is used, and the device would accordingly detect the container size by determine whether the laser had been obstructed or otherwise interfered with along its path.

It should be appreciated that the device may have a variety of different features to aid in operation. In some embodiments, the device may include a counting feature that can track how many times the machine has been used to conduct certain actions. Alternatively, a counting device may track the number of revolutions/oscillations the shaking device has performed. Such a feature may be used for maintenance anticipation and monitoring of device performance. The counter may be digital or manual. In some embodiments, the counter may be used to track how many times a specific sample has been acted upon, e.g., the counter may track how many times a specific container/vial has been activated. In some embodiments, the counter may be used to generally track how many of each type of sample has been received and acted upon.

In some embodiments, the device may include a display that can communicate a variety of different messages to a user. The display may indicate the status of the device, errors, sample type, and may alert the user to any potential problems.

Alerts may be auditory and/or visual. Examples of alerts include: alerting the user that a specific action has been performed on a sample a certain number of times, that an action has not been performed adequately or has been performed too much (e.g. shaking time was too long or too short), that the cover is open, that the container is not seated appropriately in the holder, and/or that the device requires or is soon to require maintenance. In some embodiments, the device will alert a user that the action that has been performed on the sample or container (e.g., vial) exceeded or is near the limits of an acceptable range. For example, the device may alert the user if the device performance exceeds or is near the limits on acceptable ranges for the rate or duration of shaking. As an illustrative example, the device may have shaken the sample at a rate that was too high, too low, or close to the upper or lower limit on shaking rate. The device would alert the user of this potential concern.

In some embodiments, the device will detect whether the sample is expired (e.g. by reading information from an indicator on the sample container). The device may alert the user of this and/or may prevent the device from operating while the expired sample is received by the device.

In some embodiments, the device includes an indicator portion separate from the display that indicates to a user the sample type that has been detected. The indicator may have lights that indicate sample type (e.g., aqueous or non-aqueous UCA formulation), or may have a display that displays the name of the sample type.

In some embodiments, while a user need not enter the sample type and/or the specific action to be taken, the device may ask the user to confirm the sample type that has been detected before the device can act on the sample.

The device may be powered by plugging into a wall outlet and/or may run on battery power. In some embodiments, the battery is rechargeable.

In some embodiments, the holder includes a button or other sensor to detect whether a container has been appropriately received. In some cases, the device will not operate unless it detects a container in the holder.

In some embodiments, the device may be connected to a computer or network, e.g. via Wi-Fi, USB, or other connection. This connection may be used to remotely maintain the device, e.g. patching/upgrading software and/or monitoring the device status and usage. The connection may also be used for data delivery, e.g., data obtained by the device may be sent to a database and/or printer.

In some embodiments, the device may record and transmit information such as vial usage, shaking times, temperature and other conditions, device usage, analysis results, to a database or other data storage location. In some embodiments, information from the device may be compared with databases of information to detect abnormalities with the device or the sample, and/or the comparisons may be used to categorize the sample.

In some embodiments, the device may count and monitor the amount of samples processed and/or the condition of the device and accordingly advise the user of a need to reorder items such as samples, device parts that require replacement, etc.

FIG. 1 depicts an illustrative schematic representing a device having a detector for reading an indicator from a sample container. The device 1 includes a base 60 and a cover 70. In some embodiments, the cover 70 is opened by rotationally pivoting the cover relative to the base. In some embodiments, the cover can be entirely lifted off and removed from the base. The sample container 100 to be used with the device includes an indicator 110 that indicates the type of sample in the container. The device includes a holder 10 for receiving and holding the sample container and a detector 30 for reading the indicator 110. The device also includes a shaking device 20. The device further includes a control panel 40, which includes control buttons 41 and a display 44. In some embodiments, the device may further include an indicator 50 separate from the display 44. The indicator 50 may include signals such as lights that indicate the sample type that has been detected.

Figure 2:
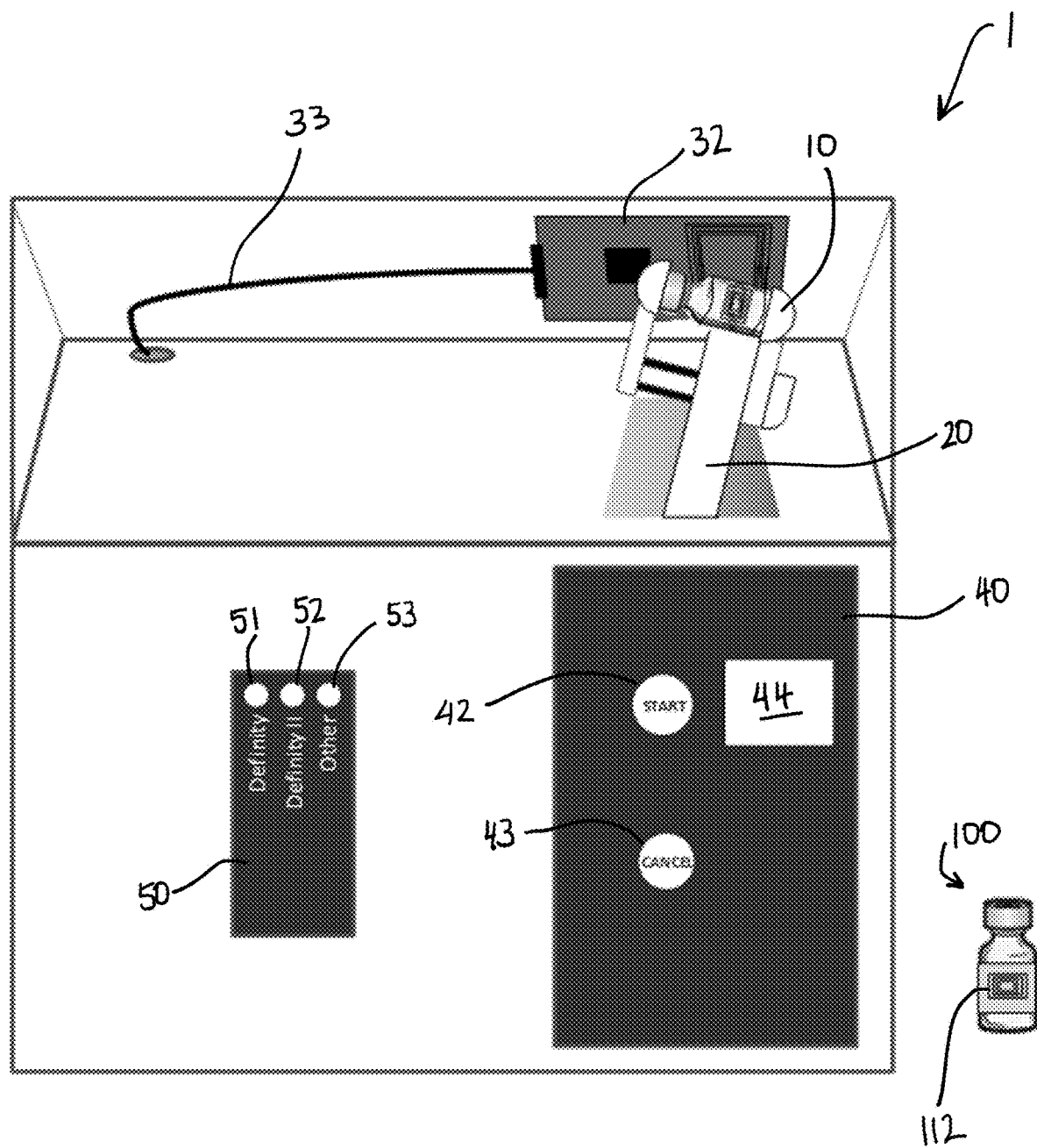
FIG. 2 is a schematic of one embodiment of a sample handling device and sample vial.

In one illustrative embodiment, shown in FIG. 2, the device 1 is used with a sample container 100 that includes an indicator in the form of a RFID tag 112. The device 1 includes an RFID reader 32 which is connected to the device via a wire 33. The sample container 100 is received by a holder 10 which is attached to a shaking arm 20. The device also includes a control panel 40 with a start button 42 and a cancel button 43, as well as a display 44. The device also includes an indicator 50 with three lights 51, 52, 53 corresponding to the three sample types. When the device detects a certain sample type, the light corresponding to that sample type lights up.

Figure 3:
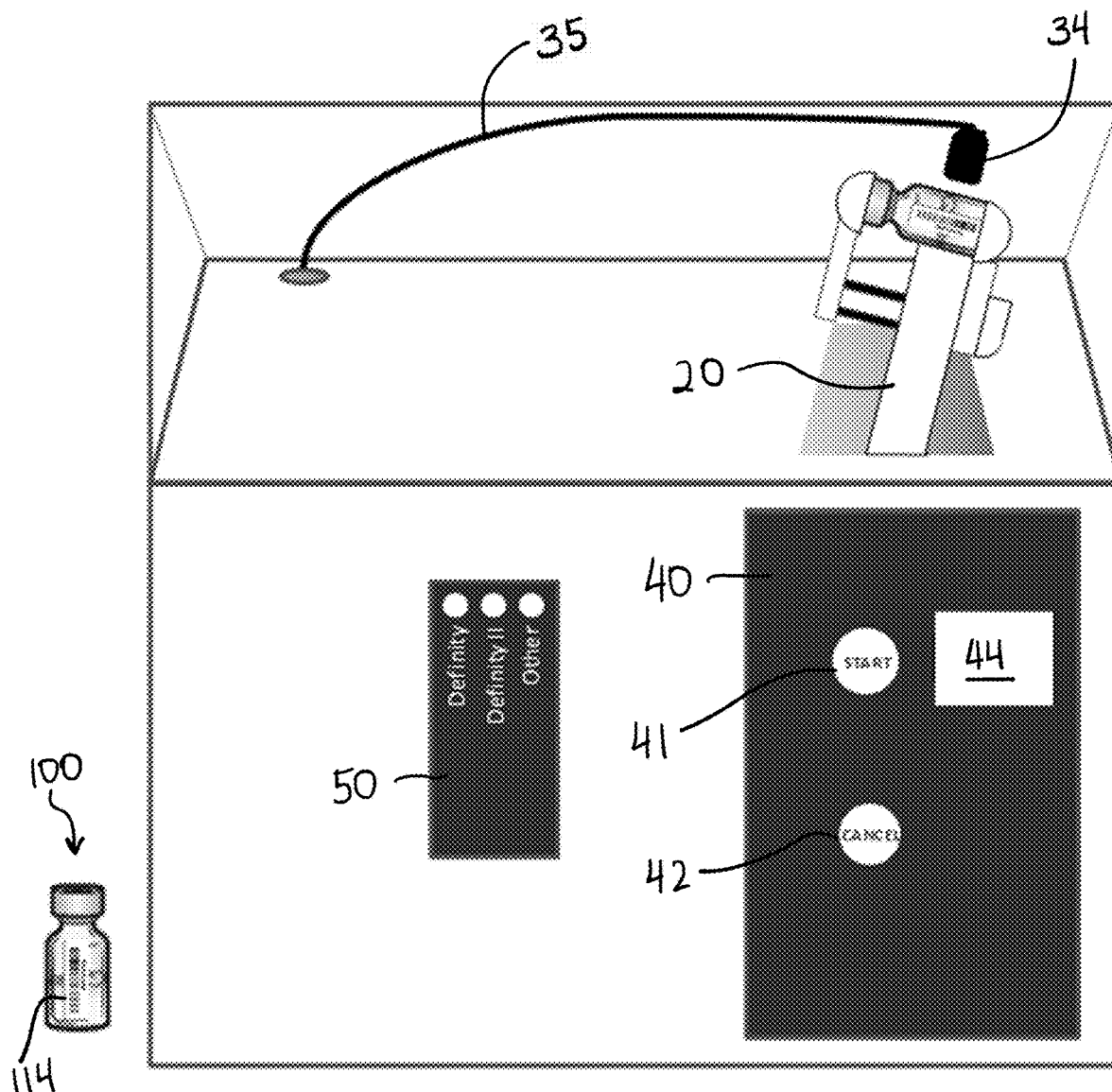
FIG. 3 is a schematic of a second embodiment of a sample handling device and sample vial.

In another illustrative embodiment, shown in FIG. 3, the device 1 is used with a sample container 100 that includes an indicator in the form of a bar code 114. The device 1 includes a bar code reader 34 which is connected to the device via a wire 35.

Figure 4:
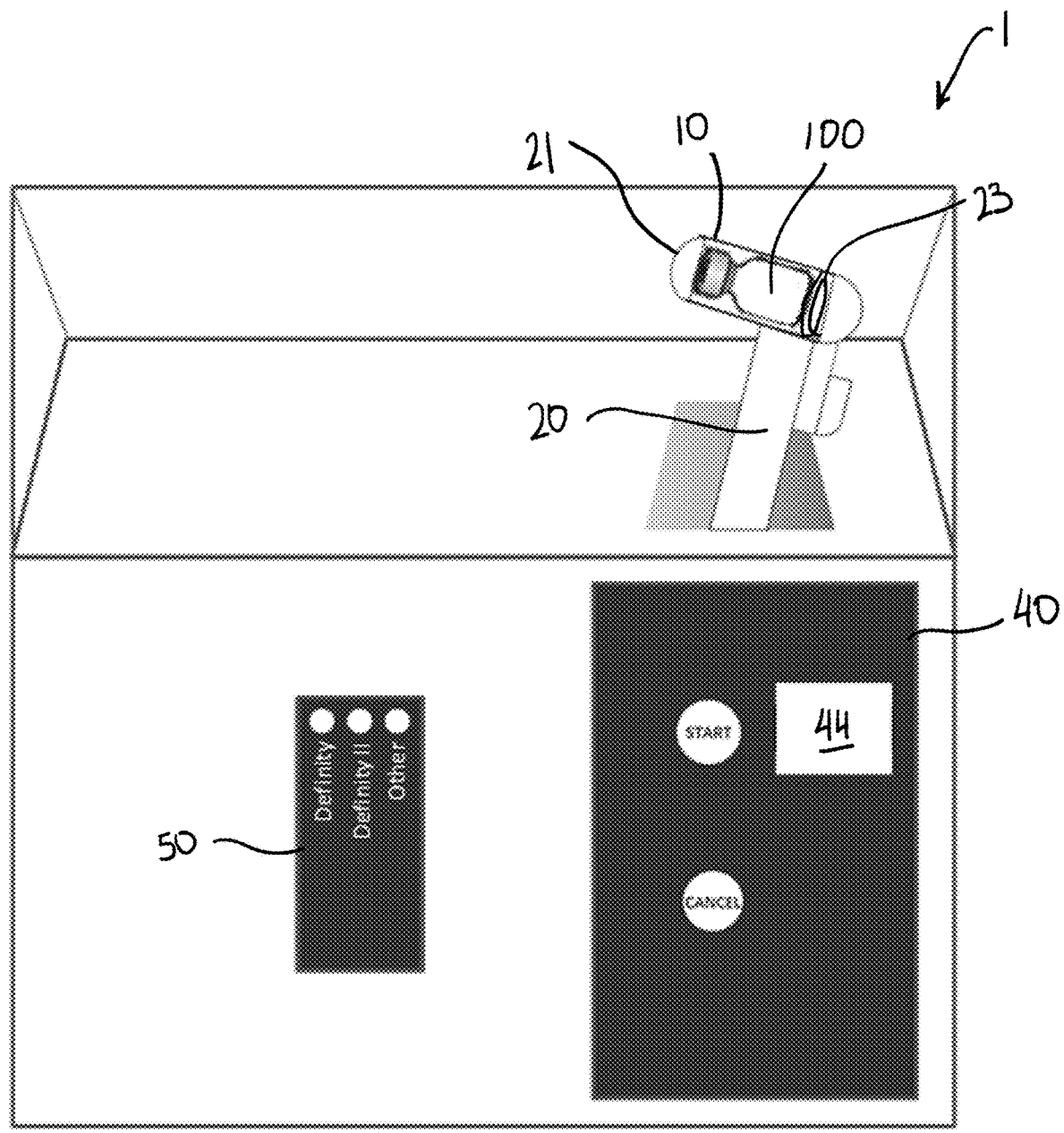
FIG. 4 is a schematic of a third embodiment of a sample handling device and sample vial

In another illustrative embodiment, shown in FIG. 4, the device 1 has a sample holder 10 that accommodates only a single container size and does not allow a larger container to fit. The sample holder 10 may have a cap cover 21 to hold the vial in place. The cap cover 21 may receive the cap of the vial and hold the vial via interference fit, a threaded arrangement (e.g. outer threads on the vial cap that mate with inner threads on the cap cover 21), mechanical interlock or any other suitable arrangement. The sample holder 10 may have a spring 23 at the base of the holder to keep the vial from moving within the holder and partially eject the vial once the cap is removed for ease of removing the vial. In some embodiments, the holder 10 can expand to accommodate a larger container, and also detect the holder size to detect the sample type, as previously discussed.

Temperature Sensors

In some embodiments, the shaking device comprises a temperature sensor that measures the temperature of the UCA formulation and/or the vial containing the UCA formulation. In some instances, the device is set to operate only when the UCA formulation or the vial containing the UCA formulation is at or about room temperature. Room temperature as used herein means a temperature of 15-30° C., including 18-25° C. and 20-25° C., and all temperatures therebetween.

Containers (e.g., Vials)

The UCA formulations may be provided in a container (or housing). In some embodiments, the container is a vial. The vial may be made of any material including but not limited to glass or plastic. The glass may be pharmaceutical grade glass. The container may be sealed with a stopper such as a rubber stopper. In some embodiments, the container is a 0.5-10 mL container. The container may be a 1-5 mL container, or a 1 or 2 mL container. Such volumes refer to the volume of liquid typically placed into the container (referred to as the liquid fill volume). This is in contrast to the entire internal volume of the container, which will be higher than the liquid fill volume. Examples of liquid fill and internal volumes are as follows: Schott 2 mL (liquid fill volume) vial having a 2.9 mL internal volume; Schott 3 mL (liquid fill volume) vial having a 4.5 mL internal volume; and Wheaton 1 mL (liquid fill volume) v-vial having a 1.2 mL internal volume.

As will be understood in the context of this disclosure, the internal volume of a container may be occupied with lipid formulation and gas. An example of a suitable container is the Wheaton 2 ml glass vial (commercially available from, for example, Nipro, Cat. No. 2702, B33BA, 2 cc, 13 mm, Type I, flint tubing vial), having an actual internal volume of about 3.75 ml. An example of a suitable stopper is a West gray butyl lyo, siliconized stopper (Cat. No. V50, 4416/50, 13 mm, WS-842). An example of a suitable seal is a West flip-off aluminum seal (Cat. No. 3766, white, 13 mm, 13-F-A-591). The containers are preferably sterile and/or are sterilized after introduction of the lipid solution and/or gas as described in published PCT application WO99/36104.

In some embodiments, the container is a flat bottom container such as a flat-bottom vial. Suitable vials include flat bottom borosilicate vials, including Wheaton vials. In some embodiments, the container is a non-flat bottom container or vial. In some embodiments, the container is a V-bottom container such as a V-bottom vial. In some embodiments, the container is a round-bottom container such as round-bottom vial. In some embodiments, the container has converging walls such that its bottom surface area (or bottom surface diameter) is smaller than its top (opening) surface area (or diameter) or smaller than any diameter therebetween (e.g., a body diameter). For clarity, a V-bottom container or vial has converging walls, and its bottom surface area is significantly smaller than any of its top or body surface areas.

It is to be understood that although some of the embodiments described herein refer to vials, they are to be read more broadly to encompass any suitable container, unless explicitly stated otherwise.

Lipids

These UCA formulations comprise one and typically more than one lipid. As used herein, "lipids" or "total lipid" or "combined lipids" means a mixture of lipids.

The lipids may be provided in their individual solid state (e.g., powdered) forms. Alternatively, the lipids may be provided as a lipid blend. Methods of making a lipid blend include those described in U.S. Pat. No. 8,084,056 and published PCT application WO 99/36104. A lipid blend, as used herein, is intended to represent two or more lipids which have been blended resulting in a more homogeneous lipid mixture than might otherwise be attainable by simple mixing of lipids in their individual powdered form. The lipid blend is generally in a powder form. A lipid blend may be made through an aqueous suspension-lyophilization process or an organic solvent dissolution-precipitation process using organic solvents. In the aqueous suspension-lyophilization process, the desired lipids are suspended in water at an elevated temperature and then concentrated by lyophilization.

The organic solvent dissolution method involves the following steps:

(a) Contacting the desired lipids (e.g., DPPA, DPPC, and MPEG5000 DPPE) with a first non-aqueous solvent system. This system is typically a combination of solvents, for example $CHCl_3$/MeOH, $CH_2Cl_2$/MeOH, and toluene/MeOH. Preferably, the first non-aqueous solvent is a mixture of toluene and methanol. It may be desirable to warm the lipid solution to a temperature sufficient to achieve complete dissolution. Such a temperature is preferably about 25 to 75° C., more preferably about 35 to 65° C. After dissolution, undissolved foreign matter may be removed by hot-filtration or cooling to room temperature and then filtering. Known methods of filtration may be used (e.g., gravity filtration, vacuum filtration, or pressure filtration).

(b) The solution is then concentrated to a thick gel/semisolid. Concentration is preferably done by vacuum distillation. Other methods of concentrating the solution, such as rotary evaporation, may also be used. The temperature of this step is preferably about 20 to 60° C., more preferably 30 to 50° C.

(c) The thick gel/semisolid is then dispersed in a second non-aqueous solvent. The mixture is slurried, preferably near ambient temperature (e.g., 15-30° C.). Useful second non-aqueous solvents are those that cause the lipids to precipitate from the filtered solution. The second non-aqueous solvent is preferably methyl t-butyl ether (MTBE). Other ethers and alcohols may be used.

(d) The solids produced upon addition of the second non-aqueous solvent are then collected. Preferably the collected solids are washed with another portion of the second non-aqueous solvent (e.g., MTBE). Collection may be performed via vacuum filtration or centrifugation, preferably at ambient temperature. After collection, it is preferred that the solids are dried in vacuo at a temperature of about 20-60° C.

The contents of U.S. Pat. No. 8,084,056 and published PCT application WO 99/36104 relating to the method of generating a lipid blend are incorporated by reference herein.

The organic solvent dissolution-precipitation process is preferred over the aqueous suspension/lyophilization process for a number of reasons as outlined in U.S. Pat. No. 8,084,056 and published PCT application WO 99/36104, including the uniformly distributed lipid solid that results using the organic dissolution method.

Alternatively, the lipids may be provided as individual powders that are dissolved together or individually directly into propylene glycol, glycerol or propylene glycol/glycerol to form the non-aqueous mixture.

As used herein, a lipid solution is a solution comprising a mixture of lipids. Similarly a lipid formulation is a formulation comprising one or more lipids. The lipids may be cationic, anionic or neutral lipids. The lipids may be of either natural, synthetic or semi-synthetic origin, including for example, fatty acids, fluorinated lipids, neutral fats, phosphatides, oils, fluorinated oils, glycolipids, surface active agents (surfactants and fluorosurfactants), aliphatic alcohols, waxes, terpenes and steroids.

At least one of the lipids may be a phospholipid, and thus the lipid blend may be referred to as a phospholipid blend. A phospholipid, as used herein, is a fatty substance containing an oily (hydrophobic) hydrocarbon chain (s) with a polar (hydrophilic) phosphoric head group. Phospholipids are amphiphilic. They spontaneously form boundaries and closed microspheres in aqueous media.

Preferably all of the lipids are phospholipids, preferably 1,2-dipalmitoyl-sn-glycero-3-phosphatidylcholine (DPPC); 1,2-dipalmitoyl-sn-glycero-3-phosphatidic acid (DPPA); and 1,2-dipalmitoyl-sn-glycero-3-phosphatidylethanolamine (DPPE). DPPA and DPPE may be provided as monosodium salt forms.

In some instances, the lipid components may be modified in order to decrease the reactivity of the microsphere with the surrounding environment, including the in vivo environment, thereby extending its half-life. Lipids bearing polymers, such as chitin, hyaluronic acid, polyvinylpyrrolidone or polyethylene glycol (PEG), may also be used for this purpose. Lipids conjugated to PEG are referred to herein as PEGylated lipids. Preferably, the PEGylated lipid is DPPE-PEG or DSPE-PEG Conjugation of the lipid to the polymer such as PEG may be accomplished by a variety of bonds or linkages such as but not limited to amide, carbamate, amine, ester, ether, thioether, thioamide, and disulfide (thioester) linkages.

Terminal groups on the PEG may be, but are not limited to, hydroxy-PEG (HO-PEG) (or a reactive derivative thereof), carboxy-PEG (COOH-PEG), methoxy-PEG (MPEG), or another lower alkyl group, e.g., as in iso-propoxyPEG or t-butoxyPEG, amino PEG (NH2PEG) or thiol (SH-PEG).

The molecular weight of PEG may vary from about 500 to about 10000, including from about 1000 to about 7500, and from about 1000 to about 5000. In some important embodiments, the molecular weight of PEG is about 5000. Accordingly, DPPE-PEG5000 or DSPE-PEG5000 refers to DPPE or DSPE having attached thereto a PEG polymer having a molecular weight of about 5000.

The percentage of PEGylated lipids relative to the total amount of lipids in the lipid solution, on a molar basis, is at or between about 2% to about 20%. In various embodiments, the percentage of PEGylated lipids relative to the total amount of lipids is at or between 5 mole percent to about 15 mole percent.

Preferably, the lipids are 1, 2-dtpalmttoyl-sn-glycero-3-phosphatidylcholine (DPPC), 1, 2-dipalmitoyl-sn-glycero-3-phosphatidic, mono sodium salt (DPPA), and N-(polyethylene glycol 5000 carbamoyl)-1, 2-dipalmitoyl-sn-glycero-3-phosphatidylethanolamine, monosodium salt (PEG5000-DPPE). The polyethylene glycol 5000 carbamoyl may be methoxy polyethylene glycol 5000 carbamoyl. In some important embodiments, the lipids may be one, two or all three of DPPA, DPPC and PEG5000-DPPE. PEG5000-DPPE may be MPEG5000-DPPE or HO-PEG5000-DPPE.

A wide variety of lipids, like those described in Unger et al. U.S. Pat. No. 5,469,854, may be used in the present process. Suitable lipids include, for example, fatty acids, lysolipids, fluorinated lipids, phosphocholines, such as those associated with platelet activation factors (PAF) (Avanti Polar Lipids, Alabaster, Ala.), including 1-alkyl-2-acetoyl-sn-glycero 3-phosphocholines, and 1-alkyl-2-hydroxy-sn-glycero 3-phosphocholines; phosphatidylcholine with both saturated and unsaturated lipids, including dioleoylphosphatidylcholine; dimyristoylphosphatidylcholine; dipentadecanoylphosphatidylcholine; dilauroylphosphatdylcholine; 1,2-dipalmitoyl-sn-glycero-3-phosphatidylcholine (DPPC); distearoylphosphatidylcholine (DSPC); and diarachidonyl-phosphatidylcholine (DAPC); phosphatidylethanolamines, such as dioleoylphosphatidylethanolamine, 1,2-dipalmitoyl-sn-glycero-3-phosphatidylethanolamine (DPPE) and distearoyl-phosphatidylethanolamine (DSPE); phosphatidylserine; phosphatidylglycerols, including distearoylphosphatidylglycerol (DSPG); phosphatidylinositol; sphingolipids such as sphingomyelin; glycolipids such as ganglioside GM1 and GM2; glucolipids; sulfatides; glycosphingolipids; phosphatidic acids, such as 1,2-dipalmitoyl-sn-glycero-3-phosphatidic acid (DPPA) and distearoyl-phosphatidic acid (DSPA); palmitic acid; stearic acid; arachidonic acid; and oleic acid.

Other suitable lipids include phosphatidylcholines, such as dioleylphosphatidylcholine, dimyristoylphosphatidylcholine, dipalmitoylphosphatidylcholine (DPPC), and distearoylphosphatidylcholine; phosphatidylethanolamines, such as dipalmitoylphosphatidylethanolamine (DPPE), dioleoylphosphatidylethanolamine and N-succinyl-dioleoyl-phosphatidylethanolamine; phosphatidylserines; phosphatidyl-glycerols; sphingolipids; glycolipids, such as ganglioside GM1; glucolipids; sulfatides; glycosphingolipids; phosphatidic acids, such as dipalmatoylphosphatidic acid (DPPA); palmitic fatty acids; stearic fatty acids; arachidonic fatty acids; lauric fatty acids; myristic fatty acids; lauroleic fatty acids; physeteric fatty acids; myristoleic fatty acids; palmitoleic fatty acids; petroselinic fatty acids; oleic fatty acids; isolauric fatty acids; isomyristic fatty acids; isopalmitic fatty acids; isostearic fatty acids; cholesterol and cholesterol derivatives, such as cholesterol hemisuccinate, cholesterol sulfate, and cholesteryl-(4'-trimethylammonio)-butanoate; polyoxyethylene fatty acid esters; polyoxyethylene fatty acid alcohols; polyoxyethylene fatty acid alcohol ethers; polyoxyethylated sorbitan fatty acid esters; glycerol polyethylene glycol oxystearate; glycerol polyethylene glycol ricinoleate; ethoxylated soybean sterols; ethoxylated castor oil; polyoxyethylene-polyoxypropylene fatty acid polymers; polyoxyethylene fatty acid stearates; 12-(((7'-diethylaminocoumarin-3-yl)-carbonyl)-methylamino)-octadecanoic acid; N-[12-(((7'-diethylamino-coumarin-3-yl)-carbonyl)-methyl-amino)octadecanoyl]-2-amino-palmitic acid; 1,2-dioleoyl-sn-glycerol; 1,2-dipalmitoyl-sn-3-succinylglycerol; 1,3-dipalmitoyl-2-succinyl-glycerol; and 1-hexadecyl-2-palmitoyl-glycerophosphoethanolamine and palmitoylhomocysteine; lauryltrimethylammonium bromide (lauryl-=dodecyl-); cetyltrimethylammonium bromide (cetryl-=hexadecyl-); myristyltrimethylammonium bromide (myristyl-=tetradecyl-); alkyldimethylbenzylammonium chlorides, such as wherein alkyl is a C.sub.12, C.sub.14 or C.sub.16 alkyl; benzyldimethyldodecylammonium bromide; benzyldimethyldodecylammonium chloride, benzyldimethylhexadecylammonium bromide; benzyldimethylhexadecylammonium chloride; benzyldimethyltetradecylammonium bromide; benzyldimethyltetradecylammonium chloride; cetyldimethylethylammonium bromide; cetyldimethylethylammonium chloride; cetylpyridinium bromide; cetylpyridinium chloride; N-[1-2,3-dioleoyloxy)-propyl]-N,N,N-trimethylammonium chloride (DOTMA); 1,2-dioleoyloxy-3-(trimethylammonio)propane (DOTAP); and 1,2-dioleoyl-e-(4'-trimethylammonio)-butanoyl-sn-glycerol (DOTB).

In some embodiments where DPPA, DPPC and DPPE are used, their molar percentages may be about 77-90 mole % DPPC, about 5-15 mole % DPPA, and about 5-15 mole % DPPE, including DPPE-PEG5000. Preferred ratios of each lipid include those described in the Examples section such as a weight % ratio of 6.0 to 53.5 to 40.5 (DPPA:DPPC:MPEG5000-DPPE) or a mole % ratio of 10 to 82 to 8 (10:82:8) (DPPA:DPPC:MPEG5000-DPPE).

Gas

The gas is preferably substantially insoluble in the lipid solutions provided herein. The gas may be a non-soluble fluorinated gas such as sulfur hexafluoride or a perfluorocarbon gas. Examples of perfluorocarbon gases include perfluoropropane, perfluoromethane, perfluoroethane, perfluorobutane, perfluoropentane, perfluorohexane. Examples of gases that may be used in the microspheres of the invention are described in U.S. Pat. No. 5,656,211 and are incorporated by reference herein. In an important embodiment, the gas is perfluoropropane.

Examples of gases include, but are not limited to, hexafluoroacetone, isopropylacetylene, allene, tetrafluoroallene, boron trifluoride, 1,2-butadiene, 1,3-butadiene, 1,2,3-trichlorobutadiene, 2-fluoro-1,3-butadiene, 2-methyl-1,3 butadiene, hexafluoro-1,3-butadiene, butadiyne, 1-fluorobutane, 2-methylbutane, decafluorobutane (perfluorobutane), decafluoroisobutane (perfluoroisobutane), 1-butene, 2-butene, 2-methy-1-butene, 3-methyl-1-butene, perfluoro-1-butene, perfluoro-1-butene, perfluoro-2-butene, 4-phenyl-3-butene-2-one, 2-methyl-1-butene-3-yne, butylnitrate, 1-butyne, 2-butyne, 2-chloro-1,1,1,4,4,4-hexafluoro-butyne, 3-methyl-1-butyne, perfluoro-2-butyne, 2-bromo-butyraldehyde, carbonyl sulfide, crotononitrile, cyclobutane, methylcyclobutane, octafluorocyclobutane (perfluorocyclobutane), perfluoroisobutane, 3-chlorocyclopentene, cyclopropane, 1,2-dimethylcyclopropane, 1,1-dimethylcyclopropane, ethyl cyclopropane, methylcyclopropane, diacetylene, 3-ethyl-3-methyldiaziridine, 1,1,1-trifluorodiazoethane, dimethylamine, hexafluorodimethylamine, dimethylethylamine, bis-(dimethyl phosphine)amine, 2,3-dimethyl-2-norbornane, perfluoro-dimethylamine, dimethyloxonium chloride, 1,3-dioxolane-2-one, 1,1,1,1,2-tetrafluoroethane, 1,1,1-trifluoroethane, 1,1,2,2-tetrafluoroethane, 1,1,2-trichloro-1,2,2-trifluoroethane, 1,1-dichloroethane, 1,1-dichloro-1,2,2,2-tetrafluoroethane, 1,2-difluoroethane, 1-chloro-1,1,2,2,2-pentafluoroethane, 2-chloro-1,1-difluoroethane, 1-chloro-1,1,2,2-tetrafluoro-ethane, 2-chloro-1,1-difluoroethane, chloroethane, chloropentafluoroethane, dichlorotrifluoroethane, fluoroethane, nitropentafluoroethane, nitrosopentafluoro-ethane, perfluoroethane, perfluoroethylamine, ethyl vinyl ether, 1,1-dichloroethylene, 1,1-dichloro-1,2-difluoroethylene, 1,2-difluoroethylene, methane, methane-sulfonylchlori-detrifluoro, methane-sulfonyl-fluoride-trifluoro, methane-(pentafluorothio)trifluoro, methane-bromo-difluoro-nitroso, methane-bromo-fluoro, methane-bromo-chloro-fluoro, methane-bromo-trifluoro, methane-chloro-difluoro-nitro, methane-chloro-dinitro, methane-chloro-fluoro, methane-chloro-trifluoro, methane-chloro-difluoro, methane-dibromo-difluoro, methane-dichloro-difluoro, methane-dichloro-fluoro, methane-difluoro, methane-difluoro-iodo, methane-disilano, methane-fluoro, methane-iodomethane-iodo-trifluoro, methane-nitro-trifluoro, methane-nitroso-triofluoro, methane-tetrafluoro, methane-trichlorofluoro, methane-trifluoro, methane sulfenylchloride-trifluoro, 2-methyl butane, methyl ether, methyl isopropyl ether, methyl lactate, methyl nitrite, methyl sulfide, methyl vinyl ether, neopentane, nitrogen (N.sub.2), nitrous oxide, 1,2,3-nonadecane tricarboxylic acid-2-hydroxycrimethyl-ester, 1-nonene-3-yne, oxygen (O.sub.2), oxygen 17 (.sup.17 O.sub.2), 1,4-pentadiene, n-pentane, dodecafluoropentane (perfluoropentane), tetradecafluorohexane (perfluorohexane), perfluoroisopentane, perfluoroneopentane, 2-pentanone-4-amino-4-methyl, 1-pentene, 2-pentene {cis}, 2-pentene {trans}, 1-pentene-3-bromo, 1-pentene-perfluoro, phthalic acid-tetrachloro, piperidine-2,3,6-trimethyl, propane, propane-1,1,1,2,2,3-hexafluoro, propane-1,2-epoxy, propane-2,2 difluoro, propane-2-amino, propane-2-chloro, propane-heptafluoro-1-nitro, propane-heptafluoro-1-nitroso, perfluoropropane, propene, propyl-1,1,1,2,3,3-hexafluoro-2,3 dichloro, propylene-1-chloro, propylene-chloro-{trans}, propylene-2-chloro, propylene-3-fluoro, propylene-perfluoro, propyne, propyne-3,3,3-trifluoro, styrene-3-fluoro, sulfur hexafluoride, sulfur (di)-decafluoro(S.sub.2 F.sub.10), toluene-2,4-diamino, trifluoroacetonitrile, trifluoromethyl peroxide, trifluoromethyl sulfide, tungsten hexafluoride, vinyl acetylene, vinyl ether, neon, helium, krypton, xenon (especially rubidium enriched hyperpolarized xenon gas), carbon dioxide, helium, and air.

Fluorinated gases (that is, a gas containing one or more fluorine molecules, such as sulfur hexafluoride), fluorocarbon gases (that is, a fluorinated gas which is a fluorinated carbon or gas), and perfluorocarbon gases (that is, a fluorocarbon gas which is fully fluorinated, such as perfluoropropane and perfluorobutane) are preferred.

The gas such as the perfluorocarbon gas is typically present below its pure concentration at room temperature due to the incorporation of air during production. The concentration of perfluoropropane when present in a vial comprising a non-aqueous mixture and a gas headspace is expected to be about 6.52 mg/mL, at about one atmosphere of pressure. The concentrations of other gases, as known in the art, would be similarly diluted due to incorporation of air during production.

The gas, such as perflutren gas, may be injected into or otherwise added to the container (e.g., the vial) comprising the solution or into the solution itself in order to provide a gas other than air. Gases that are not heavier than air may be added to a sealed container while gases heavier than air may be added to a sealed or an unsealed container.

It will be understood by one skilled in the art that a gaseous precursor may also be used, followed by conversion of the precursor into a gas either by temperature or pressure change.

Uses and Applications

The invention provides methods of use of the UCA formulations provided herein. Once activated, the UCA formulations may be used in vivo in human or non-human subjects or in vitro. The formulations provided herein may be used for diagnostic or therapeutic purposes or for combined diagnostic and therapeutic purposes.

When used as UCA for human subjects, the formulations are activated as described herein in order to form a sufficient number of gas-filled microspheres. Such microspheres may be used directly (neat) or may be diluted further in a solution, including a pharmaceutically acceptable solution, and administered in one or more bolus injections or by a continuous infusion. Administration is typically intravenous injection. Imaging is then performed shortly thereafter. The imaging application can be directed to the heart or it may involve another region of the body that is susceptible to ultrasound imaging. Imaging may be imaging of one or more organs or regions of the body including without limitation the heart, blood vessels, the cardiovasculature, the liver, the kidneys and the head.

Subjects of the invention include but are not limited to humans and animals. Humans are preferred in some instances. Animals include companion animals such as dogs and cats, and agricultural or prize animals such as but not limited to bulls and horses. UCAs are administered in effective amounts. An effective amount will be that amount that facilitates or brings about the intended in vivo response and/or application. In the context of an imaging application, such as an ultrasound application, the effective amount may be an amount of lipid microspheres that allow imaging of a subject or a region of a subject.

Software and Hardware

As discussed above, some embodiments relate to a device configured to perform different actions based on an identification of a container and/or contents of the container. To this end, a device in accordance with some embodiments may include a computer system including at least one processor programmed to perform identification of the container and/or its contents and upon determining the identification, determine appropriate actions to perform based on the identification.

Figure 5:
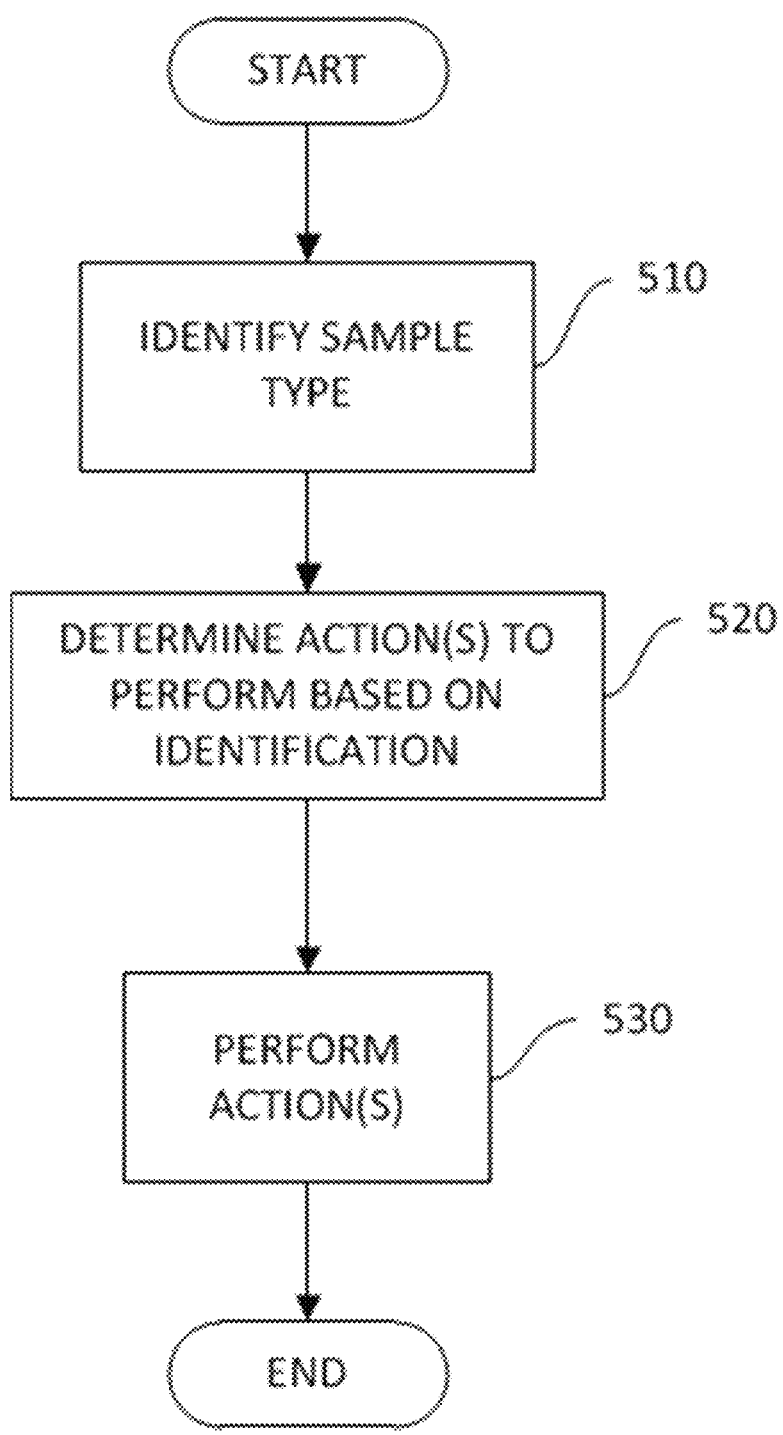
FIG. 5 is a flowchart of a process for determining action(s) to perform on a sample vial based on its identification according to one aspect.

FIG. 5 illustrates a flow chart of a process for selectively performing one or more actions to a vial placed within a device in accordance with some embodiments. In act 510, an identification of a sample type placed in the device is determined. Identification of the sample type may be determined in any suitable way, examples of which are described herein. For example, the device may present a user interface that enables a user to manually enter an identifier of the sample type. Alternatively, the device may be configured to automatically determine the sample type identification by analyzing one or more indicators located on or associated with the vial or by analyzing one or more properties of the contents of the container. In some embodiments, the device may be configured to initially automatically identify the sample type, and if such an automatic identification fails the device may provide an error message and/or prompt a user of the device to manually enter the sample type identification. Embodiments in which the sample type identification is performed manually rather than automatically may enable a less expensive and/or simpler device in which a detector (e.g., an RFID reader, an optical scanner, etc.) is not needed.

After the sample type has been identified, the process proceeds to act 520, where one or more actions to be performed on the sample are determined. In some embodiments, the device may include at least one storage device configured to store a look-up-table (LUT) or other data structure that stores information about the action(s) to be performed for particular sample type identifications. For example, a first set of actions may be performed if it is determined that the vial contains a first UCA formulation type and a second set of actions may be performed if it is determined that the vial contains a second UCA formulation type. The device may be configured to distinguish between containers with any number of different formulation types or substances contained therein, and embodiments are not limited in this respect.

Once the action(s) to be performed are determined, the process proceeds to act 530, where the at least one processor incorporated in the device instructs components of the device to perform the action(s) determined in act 520. In some embodiments, the determination to perform the action(s) may be based, at least in part, on factors other than the identification of the sample type. For example, factors such as whether a lid of the device is closed or whether the device is in a particular operating state may be considered when determining whether to perform the action(s). The at least one processor may communicate with the various components of the device to effectuate the performance of the determined action(s) in any suitable manner.

Figure 6:
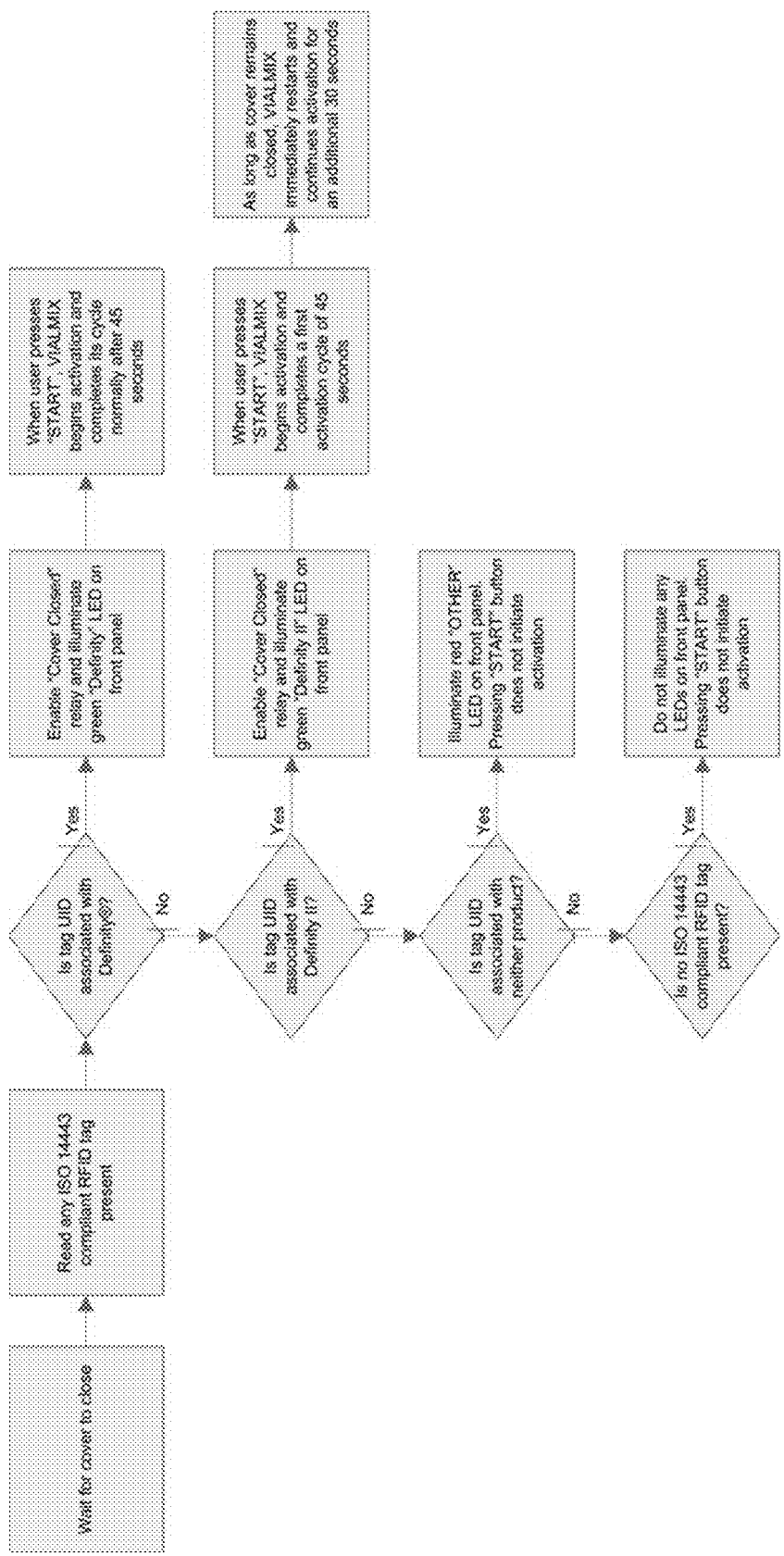
FIG. 6 is an example of the process of FIG. 5 in which the vial is identified based on an RFID tag associated with the vial.

FIG. 6 illustrates a detailed flow chart of a process for determining action(s) to perform on a sample in a vial by using RFID identification in accordance with an embodiment described in more detail below. As illustrated in FIG. 6, if an RFID tag is present on a container inserted into the device, the device reads the RFID tag to identify the container as containing a first UCA formulation type (DEFINITY®) or a second UCA formulation type (DEFINITY-II). Based on the identification and other conditions being met, the device is activated for a particular amount of time.

Figure 7:
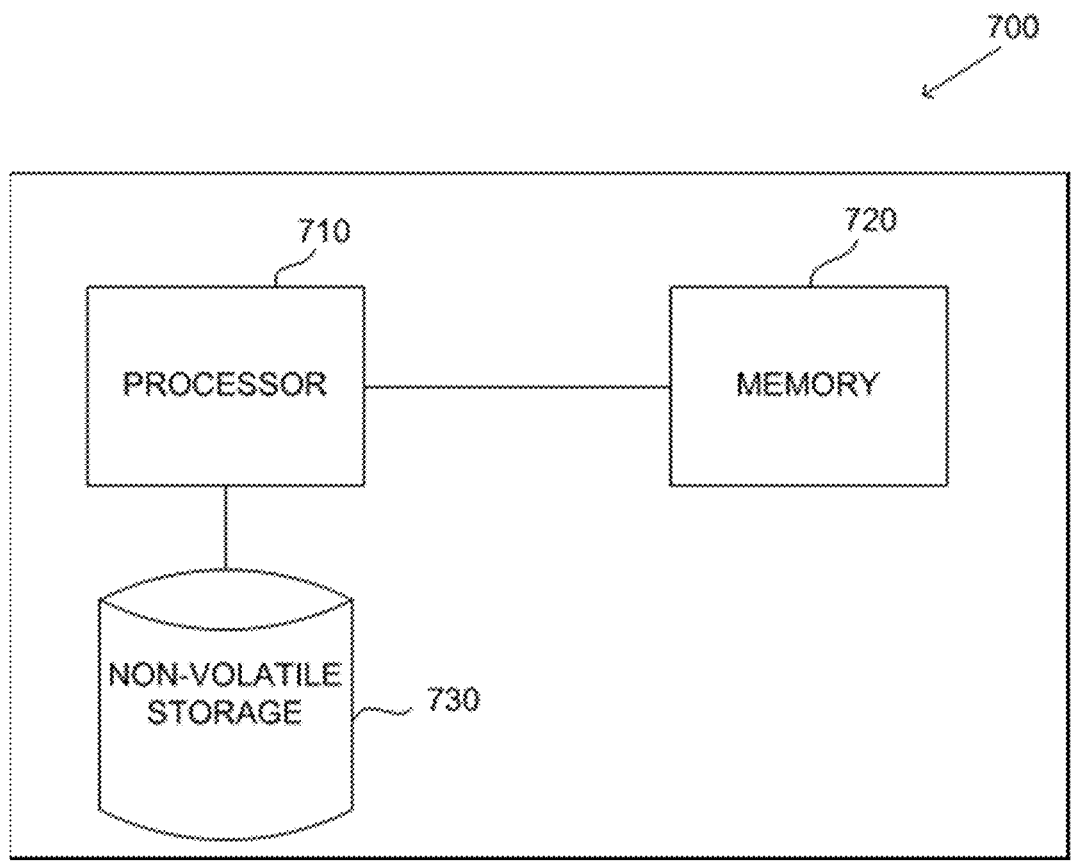
FIG. 7 is a schematic diagram of a computer system that may be included as a portion of a device for processing a sample vial according to one aspect.

An illustrative implementation of a computer system 700 that may be used in connection with any of the embodiments of the invention described herein is shown in FIG. 7. The computer system 800 may include one or more processors 710 and one or more computer-readable tangible non-transitory storage media (e.g., memory 720, one or more non-volatile storage media 730, or any other suitable storage device). The processor 710 may control writing data to and reading data from the memory 720 and the non-volatile storage device 730 in any suitable manner, as the aspects of the present invention described herein are not limited in this respect. To perform any of the functionality described herein, the processor 710 may execute one or more instructions stored in one or more computer-readable storage media (e.g., the memory 720), which may serve as tangible non-transitory computer-readable storage media storing instructions for execution by the processor 710.

The above-described embodiments of the present invention may be implemented in any of numerous ways. For example, the embodiments may be implemented using hardware, software or a combination thereof. When implemented in software, the software code can be executed on any suitable processor or collection of processors, whether provided in a single computer or distributed among multiple computers. It should be appreciated that any component or collection of components that perform the functions described above can be generically considered as one or more controllers that control the above-discussed functions. The one or more controllers can be implemented in numerous ways, such as with dedicated hardware, or with general purpose hardware (e.g., one or more processors) that is programmed using microcode or software to perform the functions recited above.

In this respect, it should be appreciated that one implementation of the embodiments of the present invention comprises at least one non-transitory computer-readable storage medium (e.g., a computer memory, a USB drive, a flash memory, a compact disk, a tape, etc.) encoded with a computer program (i.e., a plurality of instructions), which, when executed on a processor, performs the above-discussed functions of the embodiments of the present invention. The computer-readable storage medium can be transportable such that the program stored thereon can be loaded onto any computer resource to implement the aspects of the present invention discussed herein. In addition, it should be appreciated that the reference to a computer program which, when executed, performs the above-discussed functions, is not limited to an application program running on a host computer. Rather, the term computer program is used herein in a generic sense to reference any type of computer code (e.g., software or microcode) that can be employed to program a processor to implement the above-discussed aspects of the present invention.

EXAMPLES

Example 1

The commercially available, FDA-approved, aqueous based UCA formulation, DEFINITY® (Lantheus Medical Imaging, Inc.) is put into an active form ("activated") by mechanical shaking (described in U.S. Pat. No. 6,039,557, the contents of which are hereby incorporated by reference and may be used in the present process) of the PFP/lipid solution using a VIALMIX®. This results in incorporation of gas into lipid microspheres and represents the active product (see DEFINITY® prescribing information). Optimal VIALMIX® activation of DEFINITY® consistently produces gas filled microspheres that can be analyzed for number and size distribution using a particle sizer (Malvern FPIA-3000 Sysmex) when diluted with saline having lower and upper cutoffs of 1 and 80 microns.

In this experiment, DEFINITY® was activated for different periods of time and DEFINITY-II was activated for 75 seconds and the effects on microsphere mean diameter and concentration were analyzed.

Vials (Nipro Glass Americas, Nipro, Cat. No. 2702, B33BA, 2 cc, 13 mm, Type I, flint tubing vial) containing aqueous based UCA formulation (DEFINITY®) or containing non-aqueous UCA formulation (DEFINITY-II) were activated using a VIALMIX®. The microspheres formed were analyzed after reconstitution for number and size distribution using a particle sizer (Malvern FPIA-3000 Sysmex) when diluted with saline having lower and upper cutoffs of 1 and 80 microns. The activation times to achieve optimal microsphere number and equivalent diameter were different for the two products. Activation of DEFINITY® with the longer (75 sec) vs. the recommended 45 sec shake resulted in a markedly lower microsphere count but similar mean diameter. (see Tables 1 and 2).

TABLE 1

DEFINITY ® with Different Activation Times

| | DEFINITY ® @ 45 sec Activation | | DEFINITY ® @ 75 sec Activation | |
|---|---|---|---|---|
| Vial # | Mean Diameter (μm) | Count/mL × $10^9$ | Mean Diameter (μm) | Count/mL × $10^9$ |
| 1 | 1.36 | 2.56 | 1.49 | 0.86 |
| 2 | 1.35 | 2.41 | 1.52 | 0.81 |
| 3 | 1.39 | 2.64 | 1.46 | 0.89 |
| Average | 1.37 | 2.54 | 1.49 | 0.85 |

TABLE 2

DEFINITY-II

| | DEFINITY-II @75 sec Activation | |
|---|---|---|
| Vial # | Mean Diameter (μm) | Count/mL × $10^9$ |
| 1 | 1.55 | 4.95 |
| 2 | 1.49 | 5.05 |
| 3 | 1.48 | 4.74 |
| Average | 1.51 | 4.91 |

Example 2

A device which could differentiate and activate with the correct shaking period A) vials with appropriate RFID tagged aqueous based UCA formulation (DEFINITY®), B) vials with appropriately RFID tagged non-aqueous UCA formulation (DEFINITY-II) or C) vials with no tag or wrong tag was created by modifying a VIALMIX®. A diagram showing the front panel of the device is depicted in FIG. 2. The operation described in the next paragraph was effected using an RFID tag reader mounted on the interior of the device cover in close proximity to the vial holder, combined with an ATmega328P microcontroller to read RFID tags on vials in the holder and either enable or inhibit the operation of the device based on the presence or absence of a tag with a recognized unique identifier (UID) number. The RFID reader used incorporates a MFRC522 integrated circuit that is compliant with ISO/IEC 14443A standards. The tags used are "MIFARE Ultralite" in the form of self-sticking 50×15 mm labels operating at 13.56 MHz.

To activate a vial of DEFINITY® (or DEFINITY-II), the device is first turned on using the rear panel rocker switch, the cover opened and the vial is mounted in the vial holder as specified in the VIALMIX® operating instructions. The RFID tag reader is incorporated into the VIALMIX® wiring such that the shaker can only be "started" by closing the cover combined with the RFID reader identifying an appropriate tag. When a tag having a UID associated with DEFINITY® is detected, a green front panel LED labeled "DEFINITY®" is illuminated, and pressing the front panel "start" button initiates activation for a standard 45 second period. When a tag having a UID associated with DEFINITY-II is detected, a green front panel LED labeled "DEFINITY-II" is illuminated, and pressing the front panel "start" button initiates activation for a total of 75 seconds (the standard 45 second period followed by an additional activation period of 30 seconds). When an ISO 14443A-compliant RFID tag having a non-recognized UID is identified, a red LED labeled "other" is illuminated and pressing the "start" button on the front panel does not initiate activation. When no ISO 14443A-compliant RFID tag is present, no LED is illuminated and once again pressing the "start" button on the front panel does not initiate activation.

The sequence above was used in an experiment with a vial of DEFINITY® having an ISO 14443A-compliant RFID tag recognized by the microcontroller as corresponding to DEFINITY®. When the vial was put in the holder and the cover closed, the "DEFINITY®" LED was illuminated and the vial activated. Subsequent analysis using particle sizing with a Malvern FPIA-3000 Sysmex demonstrated that the microsphere size spectrum and total bubble concentration were within specification limits for activated DEFINITY® (see Table 3). Similarly, an experiment was performed with a vial of DEFINITY-II having an ISO 14443A-compliant RFID tag recognized by the microcontroller as corresponding to DEFINITY-II. When the vial was put in the holder and the cover closed, the "DEFINITY-II" LED was illuminated and the vial activated. The non-aqueous contrast agent was reconstituted with 0.9% saline and subsequently analyzed for particle number and size using a Malvern FPIA-3000 Sysmex. The testing demonstrated both DEFINITY® and DEFINITY-II bearing the appropriate RFID tag could be activated. The microsphere size was very similar to DEFINITY® and the total microsphere count approximately 1.8 fold higher.

TABLE 3

In DEFINITY ® Vial with RFID

| | DEFINITY ® @ 45 sec Activation | | DEFINITY-II @75 sec Activation | |
|---|---|---|---|---|
| Vial # | Mean Diameter (μm) | Count/mL × $10^9$ | Mean Diameter (μm) | Count/mL × $10^9$ |
| 1 | 1.36 | 2.10 | 1.60 | 3.96 |
| 2 | 1.39 | 2.41 | 1.54 | 4.48 |
| 3 | 1.36 | 2.37 | 1.49 | 4.02 |
| Average | 1.37 | 2.29 | 1.54 | 4.15 |

The front view of VIALMIX® modified for RFID recognition with RFID-tagged label vials is illustrated in FIG. 2.

Example 3

A device which could differentiate and activate with the correct shaking period A) vials with appropriate barcoded aqueous-based UCA formulation (DEFINITY®), B) vials with appropriately barcoded non-aqueous UCA formulation (DEFINITY-II) or C) vials with no barcode or wrong barcode was created by modifying a VIALMIX®. A diagram showing the front panel of the device is depicted in FIG. 3. The operation described in the next paragraph was effected using a barcode scanner in close proximity to the vial holder, combined with a computer to read barcodes on vials in the holder and either enable or inhibit the operation of the device based on the presence or absence of a barcode with a recognized identification number. The barcode scanner used was a standard keyboard-mimicking device connected via USB. Barcodes for demonstration purposes were generated online using the web site barcodesinc, generator, index.php.

To activate a vial of DEFINITY® or DEFINITY-II, the device is first turned on using the rear panel rocker switch, the cover opened and the vial is mounted in the vial holder as specified in the operating instructions. The barcode scanner is incorporated into the VIALMIX® wiring such that the shaker can only be "started" by both closing the cover and having the barcode scanner identify an appropriate barcode label. When a barcode associated with DEFINITY® is detected, pressing the front panel "start" button initiates activation. When a barcode associated with DEFINITY-II is detected, pressing the front panel "start" button also initiates activation. When a barcode having a non-recognized identifier is read, pressing the "start" button on the front panel does not initiate activation. Similarly, when no barcode is present, pressing the "start" button on the front panel does not initiate activation.

The front view of VIALMIX® modified for line/barcode scanner recognition with barcode-labeled (or tagged) vials is illustrated in FIG. 3.

Example 4

A device which could differentiate A) vials containing aqueous based UCA formulation (DEFINITY®), from B) vials containing non-aqueous UCA formulation (DEFINITY-II) was created by modifying the vial holder on a VIALMIX® shaking device. The vial holder arm on the VIALMIX® device was modified to allow a vial of limited dimensions to be held, shaken and activated to acceptable product specifications while at the same time not allowing a larger vial to fit. The differentiation of the vials was achieved by designing a holder tube to be attached to the shaker arm with a diameter that would fit a smaller vial (Schott, West Pharmaceuticals, #6800-0314) however not the larger commercial DEFINITY® vial (Nipro Glass Americas, Nipro, Cat. No. 2702, B33BA, 2 cc, 13 mm, Type I, flint tubing vial), for example. A diagram showing the vial holder is shown in FIG. 4. The non-aqueous UCA formulation was manufactured and filled into the smaller Schott vial. This vial fitted easily into the holder tube on the shaker arm with a spring at the base of the holder to keep the vial from moving within the holder, was secured with a screw on cap and activated by shaking. The aqueous UCA formulation, DEFINITY®, was manufactured and dispensed into the current commercial Nipro Glass Americas, Nipro, Cat. No. 2702, B33BA, 2 cc, 13 mm, Type I, flint tubing vial. The diameter of this vial prevented it fitting in the holder tube and prevented it from being activated. In an additional study DEFINITY® was manufactured and filled into the smaller Schott vial, placed in the holder tube and activated. The non-aqueous contrast agent in the Nipro Glass Americas, Nipro, Cat. No. 2702, B33BA, 2 cc, 13 mm, Type I, flint tubing vial would not fit in the holder tube.

An experimental study was performed using the modified tube design shaking arm and a 14.5-15 mm diameter by 35.0-35.3 mm height vial (measurements with stopper/flip top closure) with either DEFINITY® shaken for 45 seconds or DEFINITY-II shaken for 75 seconds. Subsequent analysis using particle sizing with a Malvern FPIA-3000 Sysmex demonstrated that either DEFINITY® or DEFINITY-II could be activated in the VIALMIX® with the tube design shaking arm if they were manufactured in a vial of appropriate dimensions. Consistent with prior experience after reconstitution microsphere diameters are similar but more microspheres are formed with DEFINITY-II (Table 4).

TABLE 4

With Modified Vial Holder

| | DEFINITY ® @ 45 sec Activation | | DEFINITY-II @75 sec Activation | |
|---|---|---|---|---|
| Vial # | Mean Diameter (μm) | Count/mL × $10^9$ | Mean Diameter (μm) | Count/mL × $10^9$ |
| 1 | 1.39 | 2.16 | 1.60 | 3.81 |
| 2 | 1.38 | 2.29 | 1.46 | 4.37 |
| 3 | 1.40 | 1.95 | 1.38 | 4.97 |
| Average | 1.39 | 2.13 | 1.48 | 4.38 |

The front view of VIALMIX® modified to hold vials of different shape and/or size is illustrated in FIG. 4.

Example 5

A device that could be used to change the speed of DEFINITY® and DEFINITY-II shaking was developed by replacing the AC motor in a VialMix with a Brushless DC motor (Trinamic QBL4208-100-04-025) and using a controller (TMCM-1640) and Velleman Inc. 24 volt DC power supply to control activation speed and time. In this experiment, vials (Nipro Glass Americas, Nipro, Cat. No. 2702, B33BA, 2 cc, 13 mm, Type I, flint tubing vial) containing aqueous-based UCA formulation (DEFINITY®) or containing non-aqueous UCA formulation (DEFINITY-II) were activated for different times and speeds. The microspheres formed were analyzed after reconstitution for number and size distribution using a particle sizer (Malvern FPIA-3000 Sysmex) having lower and upper cutoffs of 1 and 80 microns. The activation times for different shake speeds to achieve optimal microsphere number and equivalent diameter were different for the two products. In general, increasing the shake speed decreased the time (see Tables 5 and 6). The longer shake time required for DEFINITY-II compared to DEFINITY® could be overcome by a small increase in the shake speed. The DEFINITY® shake time could be decreased by increasing the shake speed.

TABLE 5

DEFINITY-II

| RPM | Activation Time (sec) | Diameter (gm) | Counts/mL × $10^9$ |
|---|---|---|---|
| 4900 | 120 | 1.47 | 5.54 |
| 5200 | 60 | 1.47 | 5.87 |
| 5300 | 45 | 1.61 | 4.90 |
| 5400 | 45 | 1.43 | 5.99 |
| 5500 | 35 | 1.30 | 5.83 |

TABLE 6

DEFINITY ®

| RPM | Activation Time (sec) | Diameter (gm) | Counts/mL × $10^9$ |
|---|---|---|---|
| 4300 | 45 | 1.45 | 3.39 |
| 4800 | 25 | 1.50 | 2.50 |

EQUIVALENTS

While several inventive embodiments have been described and illustrated herein, those of ordinary skill in the art will readily envision a variety of other means and/or structures for performing the function and/or obtaining the results and/or one or more of the advantages described herein, and each of such variations and/or modifications is deemed to be within the scope of the inventive embodiments described herein. More generally, those skilled in the art will readily appreciate that all parameters, dimensions, materials, and configurations described herein are meant to be exemplary and that the actual parameters, dimensions, materials, and/or configurations will depend upon the specific application or applications for which the inventive teachings is/are used. Those skilled in the art will recognize, or be able to ascertain using no more than routine experimentation, many equivalents to the specific inventive embodiments described herein. It is, therefore, to be understood that the foregoing embodiments are presented by way of example only and that, within the scope of the appended claims and equivalents thereto, inventive embodiments may be practiced otherwise than as specifically described and claimed. Inventive embodiments of the present disclosure are directed to each individual feature, system, article, material, kit, and/or method described herein. In addition, any combination of two or more such features, systems, articles, materials, kits, and/or methods, if such features, systems, articles, materials, kits, and/or methods are not mutually inconsistent, is included within the inventive scope of the present disclosure.

All definitions, as defined and used herein, should be understood to control over dictionary definitions, definitions in documents incorporated by reference, and/or ordinary meanings of the defined terms.

All references, patents and patent applications disclosed herein are incorporated by reference with respect to the subject matter for which each is cited, which in some cases may encompass the entirety of the document.

The indefinite articles "a" and "an," as used herein in the specification and in the claims, unless clearly indicated to the contrary, should be understood to mean "at least one."

The phrase "and/or," as used herein in the specification and in the claims, should be understood to mean "either or both" of the elements so conjoined, i.e., elements that are conjunctively present in some cases and disjunctively present in other cases. Multiple elements listed with "and/or" should be construed in the same fashion, i.e., "one or more" of the elements so conjoined. Other elements may optionally be present other than the elements specifically identified by the "and/or" clause, whether related or unrelated to those elements specifically identified. Thus, as a non-limiting example, a reference to "A and/or B", when used in conjunction with open-ended language such as "comprising" can refer, in one embodiment, to A only (optionally including elements other than B); in another embodiment, to B only (optionally including elements other than A); in yet another embodiment, to both A and B (optionally including other elements); etc.

As used herein in the specification and in the claims, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of," or, when used in the claims, "consisting of," will refer to the inclusion of exactly one element of a number or list of elements. In general, the term "or" as used herein shall only be interpreted as indicating exclusive alternatives (i.e. "one or the other but not both") when preceded by terms of exclusivity, such as "either," "one of," "only one of," or "exactly one of." "Consisting essentially of," when used in the claims, shall have its ordinary meaning as used in the field of patent law.

As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, as a non-limiting example, "at least one of A and B" (or, equivalently, "at least one of A or B," or, equivalently "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

It should also be understood that, unless clearly indicated to the contrary, in any methods claimed herein that include more than one step or act, the order of the steps or acts of the method is not necessarily limited to the order in which the steps or acts of the method are recited. In the claims, as well as in the specification above, all transitional phrases such as "comprising," "including," "carrying," "having," "containing," "involving," "holding," "composed of," and the like are to be understood to be open-ended, i.e., to mean including but not limited to. Only the transitional phrases "consisting of" and "consisting essentially of" shall be closed or semi-closed transitional phrases, respectively, as set forth in the United States Patent Office Manual of Patent Examining Procedures, Section 2111.03.

What is claimed is:

1. A method of using lipid-encapsulated gas microspheres for ultrasound imaging comprising:
    placing a vial comprising an ultrasound contrast agent (UCA) lipid formulation in a shaking device comprising a holder, a detector and a processor;
    determining identity of the UCA lipid formulation as either a non-aqueous UCA lipid formulation or an aqueous UCA lipid formulation based on an indicator on the vial that is read by the detector;
    selecting a shaking rate and duration from pre-set options for non-aqueous and aqueous formulations using the processor;
    activating the identified UCA lipid formulation to form lipid-encapsulated gas microspheres, by imparting a shaking pattern at the selected shaking rate and for the selected duration, using the shaking device;
    administering the lipid-encapsulated gas microspheres to a subject; and
    obtaining an ultrasound image of the subject;
    wherein the aqueous UCA lipid formulation comprises DPPA, DPPC and MPEG5000-DPPE in an aqueous solvent, and a gas,
    wherein the non-aqueous UCA lipid formulation comprises DPPA, DPPC and MPEG5000-DPPE in a non-aqueous solvent comprising propylene glycol and glycerol, and a gas, and having less than 5% water (w/w),
    wherein the detector is an RFID reader, a barcode scanner, a color scanner, or a microchip reader, and
    wherein the pre-set options comprise a shaking duration of at least 30 seconds.

2. The method of claim 1, wherein one pre-set option comprises a shaking duration of about 45 seconds and a shaking rate of at least 4000 shaking motions per minute.

3. The method of claim 1, wherein the shaking device comprises two or more holders.

4. The method of claim 1, wherein the lipid-encapsulated gas microspheres have a mean diameter of about 1-2 microns.

5. The method of claim 1, wherein the shaking device comprises a battery.

6. The method of claim 1, wherein the holder can accommodate a 35 mm tall and 14.5 mm diameter vial.

7. The method of claim 1, wherein one pre-set option comprises a shaking rate that is at least 4500 shaking motions per minute.

8. The method of claim 1, wherein one pre-set option comprises a period of time that is 45 seconds and a shaking rate that is 4530 shaking motions per minute.

9. The method of claim 8, wherein another pre-set option comprises a period of time that is 45 seconds and a shaking rate that is about 4900 shaking motions per minute.

10. The method of claim 1, wherein the shaking device further comprises at least one storage device configured to store a look-up table that stores the pre-set options.

11. The method of claim 1, wherein the indicator provides a method of use for the identified UCA lipid formulation.

12. A method of using lipid-encapsulated gas microspheres for ultrasound imaging comprising:
    placing a vial comprising an ultrasound contrast agent (UCA) lipid formulation and associated indicator in a shaking device, wherein the device comprises a holder, a detector, one or more controllers and a processor,
    reading the indicator on the vial using the detector, and identifying the vial as comprising a non-aqueous or an aqueous UCA lipid formulation based on the indicator and optionally lookup table stored in the device,
    selecting a set of activation parameters for the identified UCA lipid formulation from a first set of activation parameters for a non-aqueous UCA lipid formulation and a second set of activation parameters for an aqueous UCA lipid formulation, as programmed in the device, using the processor,
    activating the identified UCA lipid formulation to form lipid-encapsulated gas microspheres, using the selected set of activation parameters specific to the identified UCA lipid formulation using the one or more controllers, wherein activating comprises imparting a shaking pattern on the vial,
    administering the lipid-encapsulated gas microspheres to a subject, and
    obtaining an ultrasound image of the subject,
    wherein the aqueous UCA lipid formulation comprises DPPA, DPPC and MPEG5000-DPPE in an aqueous solvent, and a gas,
    wherein the non-aqueous UCA lipid formulation comprises DPPA, DPPC and MPEG5000-DPPE in a non-aqueous solvent comprising propylene glycol and glycerol, and a gas, and having less than 5% water (w/w),
    wherein the detector is an RFID detector, a barcode scanner, a color scanner, or a microchip reader, and wherein the first and the second set of activation parameters comprise a shaking time of at least 30 seconds.

13. A method of using lipid-encapsulated gas microspheres for ultrasound imaging comprising:
- placing a vial comprising an ultrasound contrast agent (UCA) lipid formulation and associated indicator in a shaking device, wherein the device comprises a holder, a detector and a processor,
- reading the indicator using the detector, and thereby distinguishing a non-aqueous UCA lipid formulation requiring activation for a first pre-determined period of time that is at least about 30 seconds and/or at a first pre-determined shaking rate that is at least 3000 shaking motions per minute from an aqueous UCA lipid formulation requiring activation for a different pre-determined period of time and/or a different pre-determined shaking rate;
- activating the non-aqueous UCA lipid formulation, by imparting a shaking pattern using the shaking device, for the first pre-determined period of time and/or at the first pre-determined shaking rate to form lipid-encapsulated gas microspheres;
- administering the lipid-encapsulated gas microspheres to a subject; and
- obtaining an ultrasound image of the subject;
- wherein the detector is an RFID detector, a barcode scanner, a color scanner, or a microchip reader, and
- wherein the non-aqueous UCA lipid formulation comprises less than 5% water (w/w).

14. The method of claim 13, wherein the non-aqueous UCA lipid formulation comprises DPPA, DPPC and MPEG5000-DPPE.

15. The method of claim 13, wherein the first pre-determined period of time is about 75 seconds.

16. The method of claim 15, wherein the first pre-determined shaking rate is about 4530 shaking motions per minute.

17. The method of claim 13, wherein the first pre-determined shaking rate is at least 4500 shaking motions per minute.

18. The method of claim 13, wherein the first pre-determined shaking rate is about 4900 shaking motions per minute.

19. The method of claim 13, wherein, upon distinguishing the non-aqueous UCA lipid formulation from the aqueous UCA lipid formulation, the shaking device automatically selects the first pre-determined period of time from at least two pre-determined periods of time.

20. The method of claim 13, wherein, upon distinguishing the non-aqueous UCA lipid formulation from the aqueous UCA lipid formulation, the shaking device automatically selects the first pre-determined shaking rate from at least two pre-determined shaking rates.

21. The method of claim 13, wherein the shaking device comprises two or more holders.

22. The method of claim 13, wherein the lipid-encapsulated gas microspheres have a mean diameter of about 1-2 microns.

23. The method of claim 13, wherein the shaking device comprises a battery.

24. The method of claim 13, wherein the holder can accommodate a 35 mm tall and 14.5 mm diameter vial.

25. The method of claim 13, wherein the non-aqueous UCA lipid formulation is activated for 45 seconds at about 4900 shaking motions per minute.

26. The method of claim 13, wherein the first pre-determined shaking rate is at least 5000 shaking motions per minute.

27. A method of using lipid-encapsulated gas microspheres for ultrasound imaging comprising:
- placing a vial comprising an ultrasound contrast agent (UCA) lipid formulation in a shaking device comprising a holder, a detector, and a processor,
- determining identity of the UCA lipid formulation as a non-aqueous UCA lipid formulation based at least in part on an indicator on the vial that is read by the detector,
- selecting a shaking rate and duration from pre-set options for a non-aqueous formulation using the processor,
- activating the identified UCA lipid formulation to form lipid-encapsulated gas microspheres, by imparting a shaking pattern at the selected shaking rate and for the selected duration, using the shaking device,
- administering the lipid-encapsulated gas microspheres to a subject; and
- obtaining an ultrasound image of the subject;
- wherein the detector is an RFID detector, a barcode scanner, a color scanner, or a microchip reader, and
- wherein the non-aqueous UCA lipid formulation comprises less than 5% water (w/w).

28. The method of claim 27, wherein the indicator provides a method of use for the identified UCA lipid formulation.

* * * * *